US009597392B2

(12) United States Patent
Pietersz

(10) Patent No.: US 9,597,392 B2
(45) Date of Patent: Mar. 21, 2017

(54) USE OF HIGH MOLECULAR WEIGHT MANNAN FOR INDUCING AND/OR ENHANCING AN IMMUNE RESPONSE

(75) Inventor: Geoffrey Alan Pietersz, Greensborough (AU)

(73) Assignee: Ascend Biopharmaceuticals Pty Ltd., South Melbourne, Victoria (AU)

( * ) Notice: Subject to any disclaimer, the term of this patent is extended or adjusted under 35 U.S.C. 154(b) by 932 days.

(21) Appl. No.: 13/696,853

(22) PCT Filed: May 10, 2011

(86) PCT No.: PCT/AU2011/000542
§ 371 (c)(1),
(2), (4) Date: Apr. 17, 2013

(87) PCT Pub. No.: WO2011/140595
PCT Pub. Date: Nov. 17, 2011

(65) Prior Publication Data
US 2013/0251741 A1    Sep. 26, 2013

Related U.S. Application Data

(60) Provisional application No. 61/333,086, filed on May 10, 2010.

(30) Foreign Application Priority Data

May 10, 2010  (AU) ................................ 2010901997
Sep. 9, 2010  (AU) ................................ 2010904060

(51) Int. Cl.
*A61K 39/395*   (2006.01)
*A61K 39/39*    (2006.01)
*A61K 39/00*    (2006.01)

(52) U.S. Cl.
CPC .... *A61K 39/39* (2013.01); *A61K 2039/55583* (2013.01)

(58) Field of Classification Search
None
See application file for complete search history.

(56) References Cited

U.S. PATENT DOCUMENTS

| | | |
|---|---|---|
| 3,362,951 A | 1/1968 | Farkas et al. |
| 4,735,935 A | 4/1988 | McAnalley et al. |
| 4,749,566 A | 6/1988 | Casellas et al. |
| 4,861,761 A | 8/1989 | Madis et al. |
| 5,308,838 A | 5/1994 | McAnalley et al. |
| 5,939,400 A | 8/1999 | Steinman et al. |
| 6,054,438 A | 4/2000 | Taylor-Papadimitriou et al. |
| 6,110,898 A | 8/2000 | Malone et al. |
| 6,222,020 B1 | 4/2001 | Taylor-Papadimitriou et al. |
| 6,280,740 B1 | 8/2001 | Gupta et al. |
| 6,573,245 B1 | 6/2003 | Marciani et al. |
| 2002/0031524 A1 | 3/2002 | Kralovec |
| 2004/0043032 A1 | 3/2004 | McKenzie et al. |
| 2004/0091491 A1 | 5/2004 | Kedl et al. |
| 2006/0084629 A1 | 4/2006 | Needleman et al. |
| 2009/0035323 A1 | 2/2009 | Stoermer et al. |
| 2010/0008951 A1 | 1/2010 | Pietersz et al. |
| 2010/0158928 A1 | 6/2010 | Stoermer et al. |
| 2010/0266491 A1 | 10/2010 | Farokhzad et al. |

FOREIGN PATENT DOCUMENTS

| | | |
|---|---|---|
| WO | WO 88/05054 | 7/1988 |
| WO | WO 93/19183 | 9/1993 |
| WO | WO 95/03825 | 2/1995 |
| WO | WO 95/20660 | 8/1995 |
| WO | WO 98/09635 | 3/1998 |
| WO | WO 98/50527 | 11/1998 |
| WO | WO 00/06723 | 2/2000 |
| WO | WO 00/63363 | 10/2000 |
| WO | WO 01/18035 | 3/2001 |
| WO | WO 01/57068 | 8/2001 |
| WO | 0203999 | 1/2002 |
| WO | WO 02/03999 | 1/2002 |
| WO | WO 2004/016643 | 2/2004 |
| WO | 2005044861 | 5/2005 |
| WO | 2005047507 | 5/2005 |
| WO | WO 2005/044861 | 5/2005 |
| WO | WO 2005/047507 | 5/2005 |
| WO | WO 2008/011672 | 1/2008 |
| WO | WO 2008/039432 | 3/2008 |
| WO | WO 2008/037033 | 4/2008 |

OTHER PUBLICATIONS

PCT International Search Report issued on Oct. 4, 2011 in connection with International Application No. PCT/AU2011/000542.
Written Opinion of the International Searching Authority issued on Oct. 4, 2011 in connection with International Application No. PCT/AU2011/000542.
Written Opinion of the International Searching Authority issued on Apr. 27, 2012 in connection with International Application No. PCT/AU2011/000542.
Written Opinion of the International Searching Authority issued on Jul. 19, 2012 in connection with International Application No. PCT/AU2011/000542.
PCT International Preliminary Report on Patentability issued on Sep. 3, 2012 in connection with PCT International Application No. PCT/AU2011/000542.
Japanese Patent Application Publication No. 2006-241020, Sep. 14, 2005, including English language translation.
Japanese Patent Application Publication No. 2006-241023, Sep. 14, 2006, including English language translation.
Agrawal and Kandimalla (2007) "Synthetic Agonists of Toll-like Receptors 7, 8 and 9", Biochem Soc Trans 35(Pt 6): 1461-1467.
Anumula (1994) "Quantitative Determination of Monosaccharides in Glycoproteins by High-Performance Liquid Chromatography with Highly Sensitive Fluorescence Detection", Analytical Biochemistry 220(2): 275-283.

(Continued)

*Primary Examiner* — Yunsoo Kim
(74) *Attorney, Agent, or Firm* — Gary J. Gershik; Cooper & Dunham LLP

(57) ABSTRACT

The present invention provides an immunostimulatory composition comprising mannans, wherein at least 75% of the mannans are greater than about 1000 kDa and/or have at least 150 aldehyde groups. The present invention also provides for the use of this composition in vaccination and gene therapy methods, together with processes for its preparation.

4 Claims, 33 Drawing Sheets

(56) References Cited

OTHER PUBLICATIONS

Figure 1:
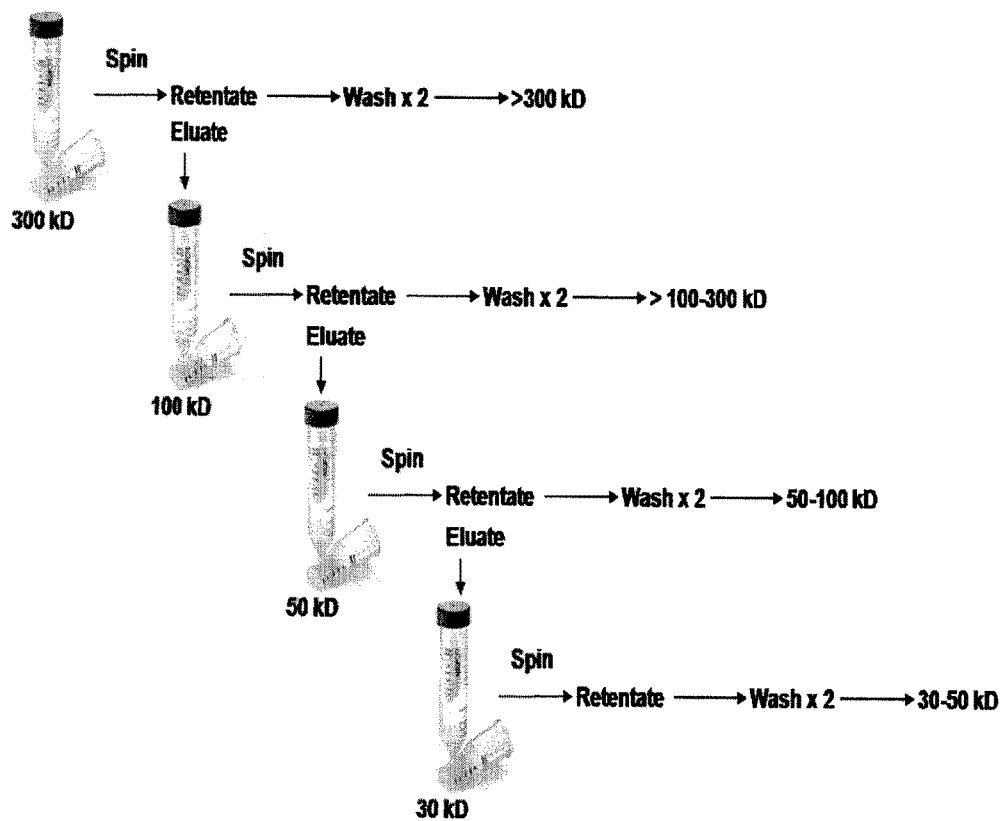

Apostolopoulos et al (1993) "Production of Anti-Breast Cancer monoclonal Antibodies Using a Glutathione-S-transferase-MUC-1 Bacterial Fusion Protein", Br J Cancer 67(4): 713-720.
Apostolopoulos et al (1995) "Oxidative/Reductive Conjugation of Manna to Antigen Selects for T1 or T2 Immune Responses", PNAS 92: 10128-10132.
Apostolopoulos et al (2000a) "Aldehyde-mannan Antigen Complexes Target the MHC Class I Antigen-Presentation Pathway", Eur J Immunol 30(6): 1714-1723.
Apostolopoulos et al (2000b) "The Evolution of DNA Vaccines", Curr Opin Mol Ther 2(4): 441-447.
Apostolopoulos et al (2006a) "Pilot Phase III Immunotherapy Study in Early-Stage Breast Cancer patient Using Oxidized Mannan-MUC1", Breast Cancer Research 8(3): R27 1-11.
Apostolopoulos et al (2006b) "Delivery of Tumor Associated Antigens to Antigen Presenting Cells Using Penetratin Induces Potent Immune Responses", Vaccine 24: 3191-3202.
Ballou (1970) "A Study of the Immunochemistry of Three Yeast Mannans", Journal of Biological Chemistry 245: 1197-1203.
Barreto-Bergter and Gorin (1983) "Structural Chemistry of Polysaccharides from Fungi and Lichens", Adv Carbohyd Chem Biochem 41: 68-103.
Bennink and Palmore (2004) "The Promise of siRNAs for the Treatment of Influenza", Trends in Molecular Medicine 10(12): 571-574.
Bystricky et al (2003) "*Candida albicans* Mannan-Protein Conjugate as Vaccine Candidate", Immunology Letters 85: 251-255.
Chalmers (2006) "Overview of New Vaccines and Technologies", Veterinary Microbiology 117: 25-31.
Cheever et al (2009) "The Prioritization of Cancer Antigens: A National Cancer Institute Pilot Program for the Acceleration of Translational Research", Clin Cancer Res 15(17): 5323-5237.
Colonna and Lampen (1974) "Structure of the Mannan from *Saccharomyces* Strain FH4C, a Mutant Constitutive for Invertase Biosynthesis. II. Protein Moiety and Components of the-Carbohydrate-Peptide Bonds", Biochemistry 13(13): 25-31.
Cox and Coulter (1997) "Adjuvants—a Classification and Review of Their Modes of Action", Vaccine 15(3): 248-256.
Czarniecki (2008) "Small Molecule Modulators of Toll-like Receptors", J Med Chem 51(21): 6621-6626.
Da Silva et al (2009) "Chemical Properties and Adjuvant Activity of a Glatactoglucomannan from *Acrocomia aculeata*", Carbohydrate Polymers 75: 380-384.
Duncan et al (2002) "Isolation of a Glactomannan That Enhances Macrophage Activation from the Edible Fungus *Morchella esculenta*", Journal of Agricultural and Food Chemistry 50(20): 5683-5685.
Durana et al (2006) "Functionalization of Mannans from Pathogenic Yeasts by Different Means of Oxidations—Preparation of Precursors for Conjugation Reactions With Respect to Preservation of Immunological Properties", Carbohydrate Polymers 63: 72-81.
Fynan et al (1993) "DNA Vaccines: Protective Immunizations by Parental, Mucosal, and Gene-Gun Inoculations", PNAS 90(24): 11478-11482.
Garulli et al (2004) "Mucosal and Systemic Immune Responses to a Human Immunodeficiency Virus Type 1 Epitope Induce Upon Vaginal Infection with a Recombinant Influenza A Virus", Journal of Virology 78: 1020-1025.
GE Healthcare Bio-Sciences AB (2002) Sweden Catalogue 18-1022-18, pp. 1-20.
Ghosh et al (2006) "Toll-like receptor (TLR) 2-9 Agonists-Induced Cytokines and Chemokines: I. Comparison with T Cell Receptor-Induced Responses", Cellular Immunology 243(1): 48-57.
Hamada et al (1984) "Structure of Cell Wall and Extracellular Mannans From *Saccharomyces rouxii* and Their Relationship to a High Concentration of NaCl in the Growth Medium", Applied and Environmental Microbiology 48(4): 708-712.
Hennessy et al (2010) "Targeting Toll-like Receptors: Emerging Therapeutics?", Nature Reviews Drug Discovery 9: 293-307.
Hofmeister et al (2006) "Tumor Stroma-Associated Antigens for Anti-Cancer Immunotherapy", Cancer Immunol Immunother 55(5): 481-494.
Kanzler et al (2007) "Therapeutic Targeting of Innante Immunity with Toll-like Receptor Agonists and Antagonists", Nature Medicine 13: 552-559.
Karanikas et al (1997) "Antibody and T Cell Responses of patients with Adenocarcinoma Immunized with Mannan-MUC1 Fusion Protein", J Clin Invest 100(11): 2783-2792.
Kim et al (2006) "Anti-Cancer Effect and Structural Characterization of Endo-Polysaccharide From Cultivated Mycelia of Inonotus Obliquus", Life Sciences 79(1): 72-80.
Koganet al (1991) "Structure of the Cell Wall Mannans of the Pathogenic Yeasts of *Candida* Species—A Complex Insight", Carbohydrate Polymers 14: 65-76.
Kurimoto et al (2010) "Synthesis and Biological Evaulation of 8-oxoadenine Derivative as Toll-Like Receptor 7 Agonists Introducing the Antedrug Concept", J Med Chem 53(7): 2964-2972.
Loveland et al (2006) "Mannan-MUC1-Pulsed Dendritic Cell Immunotheraphy: A Phase I Trial in Patients With Adenocarcinoma", Clin Cancer Res 12(3 Pt 1): 869-877.
Manna and McAnalley (1993) "Determination of the Position of the O-acetyl Group in a β-(1→4)-manna (Acemannan) from *Aloe barbardensis* Miller", Carbohydrate Research 241: 317-319.
Masarova et al (2001) "Stability Enhancement of *Escherichia coli* Penicillin G Acylase by Glycosylation With Yeast Mannan", Biotechnol Appl Biochem 34(Pt 2): 127-133.
Monsigny et al (1988) "Colorimetric Determination of Neutral Sugars by a Resoscinol Sulfuric Acid Micromethod", Analytical Biochemistry 175: 525-530.
Nakajima and Ballou (1974) "Characterization of the Carbohydrate Fragments Obtained from *Saccharomyces cerevisiae* Mannan by Alkaline Degradation", Journal of Biological Chemistry 249(23): 7679-7684.
Neri and Bicknell (2005) "Tumour Vascular Targeting", Nature Reviews Cancer 5: 436-446.
Pardoll and Allison (2004) "Cancer Immunotherapy: Breaking the Barrier to Harvest the Crop", Nature Medicine 10(9): 887-892.
Petrovsky and Aguilar (2004) "Vaccine Adjuvants: Current State and Future Trends", Immunology and Cell Biology 82: 488-496.
Philbin and Levy (2007) "Immunostimulatory Activity of Toll-like Receptor 8 Agonists Towards Human Leucocytes: Basic Mechanisms and Translational Opportunities", Biochem Soc Trans 35(Pt 6): 1485-1491.
Pietersz et al (2006) "Design of Peptide-Based Vaccines for Cancer", Current Medicinal Chemistry 13(14): 1591-1607.
Pugh et al (2001) "Characterization of Aloeride, A New High-Molecular-Weight Polysaccharide from Aloe vera With Potent Immunostimulatory Activity", J Agric Food Chem 49(2): 1030-1034.
Qiu et al (2000) "Modified Aloe Barbadensis Polysaccharide with Immunoregulatory Activity", Planta Med 66(2): 152-156.
Sasaki et al (1997) "Human Immunodeficiency Virus Tyoe-1-Specific Immune Responses Induced by DNA Vaccinations Are Greatly Enhanced by Manna-Coated diCl4-amidine", Eur J immunol 27(12): 3121-3129.
Sharma et al (2003) "A Simple Polyacrylamide Gel Electrophoresis Procedure for Separation of Polyamidoamine Dendrimers", Electrophoresis 24(16): 2733-2739.
Shedlock and Weiner (2000) "DNA Vaccination: Antigen Presentation and the Induction of Immunity", Journal of Leukocyte Biology 68: 793-806.
Sheng et al (2005) "Dendritic Cells: Activation and Maturation—Applications for Cancer Immunotherapy", Current Medicinal Chemistry 12(15): 1783-1800.
Sheng et al (2006) "Mannan Derivatives Induce Phenotypic and Functional Maturation of Mouse Dendritic Cells", Immunology 118(3): 372-383.
Shibata et al (1983) "Isolation of Mannan-Protein Complexes From Viable Cells of *Saccharomyces cerevisiae* X2180-1A Wild Type and *Saccharomyces cerevisiae* X2180-1A-5 Mutant Strains by the Action of Zymolyase-60,000", Journal of Bacteriology 156(2): 552-558.

(56) References Cited

OTHER PUBLICATIONS

Shukla et al (2010) "Structure-Activity Relationships in Human Toll-Like Receptor 7-active Imidazoquinoline Analogues", J Med Chem 53(11): 4450-4465.

Sutcliffe et al (1983) "Antibodies That React With Predetermined Sites on Proteins", Science 219(4585): 660-666.

Tang et al (2006) "Mannan-Mediated Gene Delivery for Cancer Immunotherapy", Immunology 120: 325-335.

Tang et al (2008) "Oxidized and Reduced Mannan Mediated MUC1 DNA Immunization Induce Effective Anti-Tumor Responses", Vaccine 26(31): 3827-3834.

Tang et al (2007) "Molecular Basis of Improved Immunogenicity in DNA Vaccination Mediated by a Mannan Based Carrier", Biomaterials 30(7): 1389-1400.

Tomai et al (2007) "Resiquimod and Other Immune Response Modifier as Vaccine Adjuvants", Expert Rev Vaccines 6(5): 835-847.

Van der Bruggen et al (1991) "A Gene Encoding an Antigen Recognized by Cytolytic T Lymphocytes on a Human Melanoma", Science 254(5038): 1643-1647.

Van Ginkel et al (2000) "Vaccines for Mucosal Immunity to Combat Emerging Infectious Diseases", Emerging Infectious Diseases 6: 123-132.

Vinogradov et al (1998) "Structural Analysis of the Intact Polysaccharide Manna from *Saccharomyces cerevisiae* yeast using $^1$H and $^{13}$C NMR Spectroscopy at 750 MHz", Carbohydrate Research 307: 177-183.

Wang et al (2007) "Compositional Monosaccharide Analysis of Transgenic Corn Glycoproteins by HPLC With Fluorescence Detection and LC-MS With Sonic Spray Ionization", Journal of Chromatographic Science 45: 200-206.

Xin et al (2008) "Synthetic Glycopeptide Vaccines Combining β-Mannan and Peptide Epitopes Induce Protection Against Candidiasis", PNAS 105: 13526-13531.

Zuany-Amorim et al (2002) "Toll-Like Receptors as Potential Therapeutic Targets for Multiple Diseases", Nature Reviews Drug Discovery 1: 797-807.

Extended European Search Report issued on Oct. 22, 2013 in connection with European Patent Application No. EP11779973.4.

International-Type Search Report issued on Jun. 25, 2010 in connection with Australian Patent No. AU2010901997.

Feb. 8, 2016 Second Office Action, issued in connection with Japanese Patent Application No. 2013-509404, including English Language Translation.

Product Name  Mannan from Saccharomyces cerevisiae, powder
Product Number  M7504
Product Brand  SIGMA
CAS Number  9036-88-8

| TEST | SPECIFICATION | LOT 048K3810 RESULTS |
|---|---|---|
| APPEARANCE | WHITE TO LIGHT YELLOW WITH A BROWN CAST POWDER | LIGHT YELLOW POWDER |
| SOLUBILITY | CLEAR TO SLIGHTLY HAZY YELLOW TO TAN SOLUTION AT 50MG/ML IN WATER | SLIGHTLY HAZY LIGHT YELL |
| CARBON | REPORT RESULT | 40.3% (39.7%) |
| PHOSPHORUS | REPORT RESULT | 0.6% (0.5%, 0.2%) |
| SODIUM | REPORT RESULT | 0.9% (0.7%, 0.67%, 2.3%) |
| SPECIFIC ROTATION | +73 TO +82DEG (C=1 IN WATER) | +78 DEG (+80, 75.7, 78.5, 74) |
| THIN LAYER CHROMATOGRAPHY | NO LOW MOLECULAR WEIGHT SACCHARIDES DETECTED | CONFORMS |
| RECOMMENDED RETEST | 2 YEARS | MAY 2010 |
| QC RELEASE DATE | | MAY 2008 |

Figure 18

| Batch no & size | no. of residues | | |
|---|---|---|---|
| | 1. | 2. | 3. |
| 102K3778 large | 153 | 129 | 125 |
| 102K37781 large | 148 | 128 | 131 |
| 92H3876 small | 101 | 100 | 106 |
| 92H3876 medium | - | 97 | 98 |
| 16H3843 medium | - | 92 | 100 |

Figure 20

USE OF HIGH MOLECULAR WEIGHT MANNAN FOR INDUCING AND/OR ENHANCING AN IMMUNE RESPONSE

RELATED APPLICATIONS

This application is a §371 national stage of PCT International Application No. PCT/AU2011/000542, filed May 10, 2011, claiming priority of Australian Patent Application Nos. 2010904060, filed Sep. 9, 2010 and 2010901997, filed May 10, 2010 and U.S. Provisional Application 61/333,086, filed May 10, 2010, the contents of each of which are hereby incorporated by reference into this application.

FIELD OF THE INVENTION

The present invention relates to carbohydrate polymers comprising mannose, particularly mannans, their preparation and use in immunostimulatory and vaccine compositions.

REFERENCE TO A SEQUENCE LISTING

This application incorporates-by-reference nucleotide and/or amino acid sequences which are present in the file named "130531_5938_84666_Substitute_Sequence_ Listing_SC.txt", which is 817 bytes in size, and which was created May 31, 2013 in the IBM-PC machine format, having an operating system compatibility with MS-Windows, which is contained in the text file filed May 31, 2013 as part of this application.

BACKGROUND OF THE INVENTION

Several polysaccharides (carbohydrate polymers) of mannose (e.g., mannans), β(1,3) glucose (e.g., glucans), β(1,4) acetylated mannose (acemannans), β(1,4) N-acetyl-glucosamine (chitins), and heteropolysaccharides, such as rhamnogalacturonans (pectins), have been shown to stimulate the immune system.

Binding of polysaccharides to C-type lectin receptors induces immunostimulation, as shown by the increase in phagocytosis, proliferative responses, release of cytokines, and other activities of the immune system. Because of this immunostimulatory activity, these polysaccharides have been proposed for use in vaccine compositions. Of particular interest is mannan.

Mannan is a polymannose recognized by C-type lectin receptors, such as the mannose receptor (CD206) and DC-SIGN (CD209). Because of their presence on antigen-presenting cells, these receptors have been characterized for their uptake of mannose, fucose or glucose containing compounds. Binding of mannan to the mannose receptor for instance, induces endocytosis, followed by its delivery into the endosomal pathway. Early studies on mannnosylated antigens indicated that the presence of mannose residues on antigens greatly enhanced antigen-uptake and major histocompatibility complex (MHC) class II-restricted antigen presentation by dendritic cells (DCs). Conjugation of mannan to at least one antigen also enhances its uptake and presentation.

Although the immunostimulatory properties of certain polysaccharides have been known for some time, their use has been largely limited to research applications. This is due in part, to the strict regulations governing their use in a clinical setting, particularly with regard to humans. As a result, there is a need for further immunostimulatory and vaccine compositions for use in the treatment or prevention of diseases, as well as reliable methods for the preparation thereof.

SUMMARY OF THE INVENTION

Whilst endeavouring to devise methods for producing compositions comprising carbohydrate polymers comprising mannose with reproducible characteristics for therapeutic use, the present inventors were surprised to find that a sub-population of mannans with a defined size and/or aldehyde content have enhanced properties when compared with other sub-populations, as well as compared to the starting population.

Thus, in a first aspect the present invention provides an immunostimulatory composition comprising mannans, wherein at least 75% of the mannans are greater than about 1000 kDa.

In an embodiment, the mannans are oxidized and hence comprise aldehyde groups. This is particularly useful when the mannans are to be conjugated to at least one antigen or nucleic acid encoding therefor.

In an embodiment, the size distribution of the mannans following labelling with aminonaphthalene-1,3,6-trisulfonic acid (ANTS) is between about 150 to about 250 Da based on protein standards and/or is between about 800 to about 3000 kDa based on carbohydrate standards.

In another aspect, the present invention provides an immunostimulatory composition comprising oxidized mannans, wherein at least 75% of the mannans have at least 150 aldehyde groups.

In another aspect, the present invention provides an immunostimulatory composition comprising oxidized mannans, wherein at least 75% of the mannans are greater than about 1000 kDa and have at least 150 aldehyde groups.

Furthermore, provided is a vaccine composition comprising mannans and at least one antigen or nucleic acid encoding therefor, wherein at least 75% of the mannans are greater than about 1000 kDa.

In an embodiment, the mannans are oxidized.

In a further embodiment, the oxidized mannans are covalently conjugated to the at least one antigen.

In an alternate embodiment, the oxidized mannans are conjugated to the at least one nucleic acid via polycations.

In an embodiment, at least 75% of the oxidized mannans have at least 150 aldehyde groups prior to being conjugated to the at least one antigen or nucleic acid encoding therefor.

In an embodiment, the size distribution of the mannans prior to conjugation to the antigen or nucleic acid encoding therefor and following labelling with aminonaphthalene-1, 3,6-trisulfonic acid (ANTS) is between about 150 to about 250 Da based on protein standards and/or is between about 800 to about 3000 kDa based on carbohydrate standards.

The mannans can be from any source, such as fungi, more preferably yeast.

The antigen can be from any source such as viral, bacterial, protozoan, fungal, tumor antigen, a self antigen, or an allegen. The antigen may be, for example, a whole organism, a protein, or an antigenic peptide.

In an embodiment, a composition of the invention is formulated for mucosal, topical, intradermal, intramuscular, subcutaneous, or intravenous administration.

In an embodiment, a composition of the invention further comprises at least one acceptable carrier.

In another aspect, the present invention provides a method for inducing and/or enhancing an immune response in a subject, the method comprising administering to the subject a composition of the invention.

In an embodiment, the method comprises administering the at least one antigen or a nucleic acid encoding therefor.

In an embodiment, the mannans and the at least one antigen or the nucleic acid are administered sequentially or simultaneously. In a preferred embodiment, they are administered in the same composition.

In an embodiment, the mannans and the at least one antigen or nucleic acid encoding therefor are administered as a vaccine composition according to the invention.

In an embodiment, when the antigen is from an infectious agent or is a mutant/derivative thereof, the method immunizes the subject against a pathogen (infectious agent). In another embodiment, when the antigen is from a cancer cell or is a mutant/derivative thereof, the method is for cancer therapy.

In an embodiment, the composition is administered mucosally, topically, intradermaly, intramuscularly, subcutaneously, or intravenously.

Also provided is the use of a composition of the invention for the manufacture of a medicament for inducing and/or enhancing an immune response in a subject.

Further, provided is the use of a composition of the invention for inducing and/or enhancing an immune response in a subject.

The compositions of the invention can also be used in in vitro or ex vivo priming methods. Accordingly, in a further aspect the present invention provides a method for activating macrophages, DCs and/or cytotoxic T lymphocytes (CTLs) in vitro or ex vivo, the method comprising contacting the cells with a composition of the invention. The primed cells can be administered to a subject in need.

The mannan population of the invention selected on size and or aldehyde content can also be used to deliver at least one nucleic acid to a cell. Thus, in a further aspect, the present invention provides a composition for delivering at least one nucleic acid to a cell, the composition comprising the at least one nucleic acid and mannans, wherein at least 75% of the mannans are greater than about 1000 kDa.

In an embodiment, the mannans are oxidized.

In a further embodiment, the oxidized mannans are conjugated to the at least one nucleic acid via polycations.

In a further embodiment, at least 75% of the oxidized mannans have at least 150 aldehyde groups prior to being conjugated to the at least one nucleic acid.

In another aspect, the present invention provides a method for delivering at least one nucleic acid to a cell, the method comprising contacting the cell with the composition of the above aspect.

In an embodiment, the cell is in vitro or ex vivo. In an alternate embodiment, the cell is in vivo.

In an embodiment, the nucleic acid is delivered to the cell for gene therapy or genetic vaccination.

Also provided is the use of the composition for the manufacture of a medicament for gene therapy or genetic vaccination.

Further, provided is the use of the composition for gene therapy or genetic vaccination.

In another aspect the present invention provides a process for preparing a composition of the invention, the process comprising
i) obtaining a composition comprising mannans,
ii) fractionating the composition from step i) based on size,
iii) selecting one or more fractions comprising mannans, wherein at least 75% of the mannans in the one or more fractions are greater than about 1000 kDa, and
iv) optionally admixing the fraction from step iii) with at least one other compound.

In an embodiment, the process further comprises the step of oxidizing the mannans prior to step iv). In a further embodiment, at least 75% of the oxidized mannans have at least 150 aldehyde groups.

In an embodiment, the at least one other compound is an antigen or a nucleic acid encoding therefor.

In another aspect, the present invention provides a process for preparing the vaccine composition of the invention, the process comprising
i) obtaining a composition comprising mannans, wherein at least 75% of the mannans are greater than about 1000 kDa; and
ii) admixing or conjugating the composition from step i) with at least one antigen or a nucleic acid encoding therefor, to thereby prepare the vaccine composition.

In an embodiment, the process further comprises oxidizing the mannans prior to step ii). In a further embodiment, at least 75% of the oxidized mannans have at least 150 aldehyde groups.

To assist in the production of compositions of the invention and more generally, compositions comprising a carbohydrate polymer comprising mannose, it is preferable that the starting population(s) of the carbohydrate polymer comprising mannose (for example, mannan) is consistent between batches and/or has a sufficiently high representation of larger molecular weight species of the carbohydrate polymer.

Accordingly, in another aspect, the present invention provides a process for selecting a composition comprising a carbohydrate polymer comprising mannose, the process comprising
i) obtaining a composition comprising a carbohydrate polymer comprising mannose,
ii) analyzing the size distribution and/or aldehyde content of the composition from step i), and
iii) selecting the composition if it comprises a desired size distribution and/or aldehyde content.

In an embodiment, the size distribution is analyzed by
i) oxidizing a portion of the composition,
ii) labelling the oxidized product from step i) with ANTS, and
iii) analyzing the size distribution by resolving the ANTS labelled product from step ii) by SDS-PAGE.

In an embodiment, the aldehyde content is analyzed by
i) oxidizing a portion of the composition,
ii) reacting the oxidized product from step i) with 3-(2-pyridyldithio)propionyl hydrazide (PDPH),
iii) reacting the product from step ii) with a reducing agent to release 2-pyridinethione, and
iv) measuring the release of 2-pyridinethione.

In an embodiment, the reducing agent is dithiothreitol (DTT).

In an embodiment, the release of 2-pyridinethione is measured by spectrophotometry at an absorbance of OD343 nm.

In an embodiment, the composition is oxidized with sodium periodate.

In an embodiment, the process further comprises determining the purity of the composition from step i). For example, the purity can be determined by quantitating the sugar content of the carbohydrate polymer by i) reacting the composition with resorcinol (1,3-dihydroxybenzene) in the presence of hydrated sulphuric acid, ii) measuring the absorbance at OD430-480 nm, and iii) comparing the absorbance against a standard.

Good manufacturing practice for pharmaceutical products is an important requirement to obtain regulatory approval. However, the source of many, if not all, compositions comprising carbohydrate polymers comprising mannose results in highly heterogeneous populations making them difficult to clearly and consistently define. This is particularly the case for polymers obtained from natural sources such as yeast. Not only have the present inventors identified a new composition comprising mannans with enhanced properties, the invention also provides a process for producing such compositions and more generally, compositions comprising a carbohydrate polymer comprising mannose, with well defined properties, making them more amenable to the regulatory approval process.

Accordingly, in another aspect the present invention provides a process for preparing a composition comprising a carbohydrate polymer comprising mannose, the process comprising i) obtaining a composition comprising a carbohydrate polymer comprising mannose, wherein the carbohydrate polymer comprises aldehyde groups, ii) fractionating the composition based on size, and iii) selecting one or more fractions comprising the carbohydrate polymer with a desired size distribution from step ii) to thereby prepare the composition.

Alternatively, the process comprises i) obtaining a composition comprising a carbohydrate polymer comprising mannose, ii) fractionating the composition based on size, iii) oxidizing one or more fractions obtained from step ii), and iv) selecting one or more fractions comprising the carbohydrate polymer with a desired size distribution and/or aldehyde content from step iii) to thereby prepare the composition.

In an embodiment of the alternate process, the one or more fractions are oxidized with sodium periodate.

In an embodiment of the alternate process, before step ii), the composition is selected using a method of the invention.

Step ii) for either process can be carried out using any suitable method such as, but not limited to, tangential flow filtration, size exclusion chromatography and/or ultrafiltration.

In another embodiment, either process further comprises analyzing the aldehyde content of the one or more fractions prior to selection. In an embodiment, the aldehyde content is analysed by i) reacting a portion of the one or more fractions with PDPH, ii) reacting the product from step i) with a reducing agent to release 2-pyridinethione, and iii) measuring the release of 2-pyridinethione.

In an embodiment, the reducing agent is DTT.

In an embodiment, the release of 2-pyridinethione is measured by spectrophotometry at an absorbance of OD343 nm.

In a further embodiment, either process further comprises analyzing the size distribution of the selected one or more fractions. For example, the size distribution can be analyzed by i) labelling a portion of the one or more fractions with ANTS, and ii) analyzing the size distribution by resolving the one or more ANTS labelled fractions from step (i) by SDS-PAGE.

In an embodiment, the carbohydrate polymer comprising mannose is mannan, and a) the molecular weight of the mannan in the selected fraction is greater than about 1000 kDa, and the size distribution following labelling with ANTS is between about 150 to about 250 Da based on protein standards and/or is between about 800 to about 3000 kDa based on carbohydrate standards, b) the molecular weight of the mannan in the selected fraction is between about 300 to about 1000 kDa, and the size distribution following labelling with ANTS is between about 150 to about 175 Da based on protein standards and/or is between about 400 to about 1000 kDa based on carbohydrate standards, c) the molecular weight of the mannan in the selected fraction is between about 100 to about 300 kDa, and the size distribution following labelling with ANTS is between about 80 to about 125 Da based on protein standards and/or is between about 90 to about 400 kDa based on carbohydrate standards, d) the molecular weight of the mannan in the selected fraction is between about 50 to about 100 kDa, and the size distribution following labelling with ANTS is between about 60 to about 80 Da based on protein standards and/or is between about 50 to about 175 kDa based on carbohydrate standards, or e) the molecular weight of the mannan in the selected fraction is between about 30 to about 50 kDa, and the size distribution following labelling with ANTS is between about 50 to about 60 Da based on protein standards and/or is between about 20 to about 50 kDa based on carbohydrate standards.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying Figures.

BRIEF DESCRIPTION OF THE ACCOMPANYING DRAWINGS

FIG. 1: Fractionation process using Centriprep concentrators.

Figure 2:
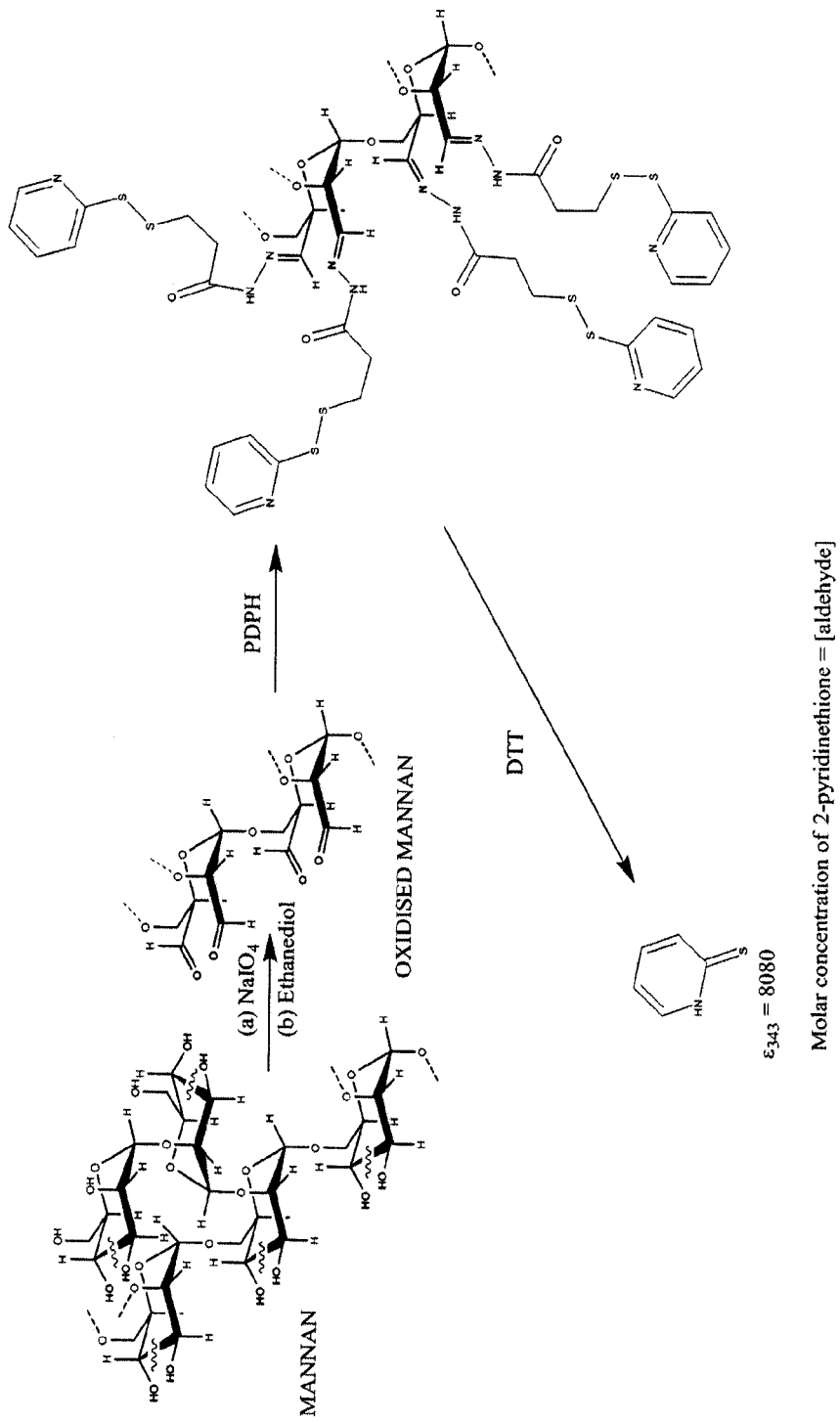

FIG. 2: Schematic depicting method for quantitating aldehyde residues in oxidized mannan.

Figure 3:
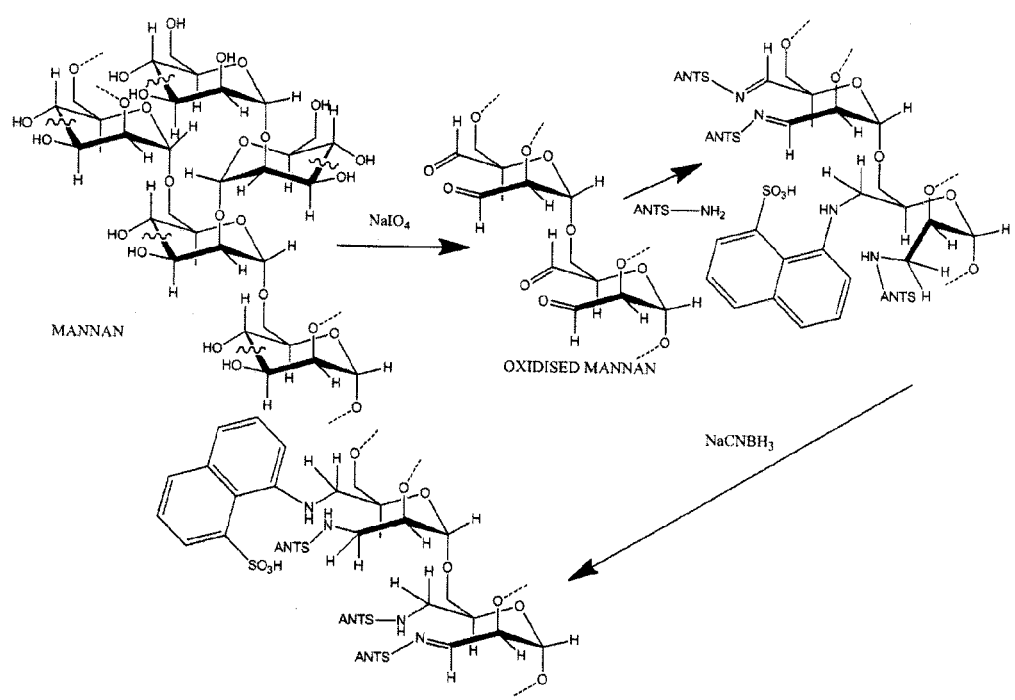

FIG. 3: Schematic depicting the modification of oxidized mannan with ANTS.

Figure 4:
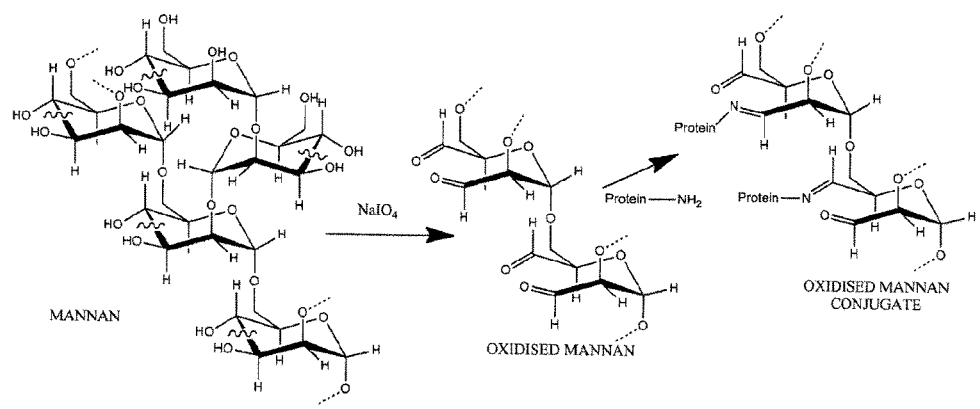

FIG. 4: Scheme depicting conjugation of proteins to oxidized mannan.

Figure 5:
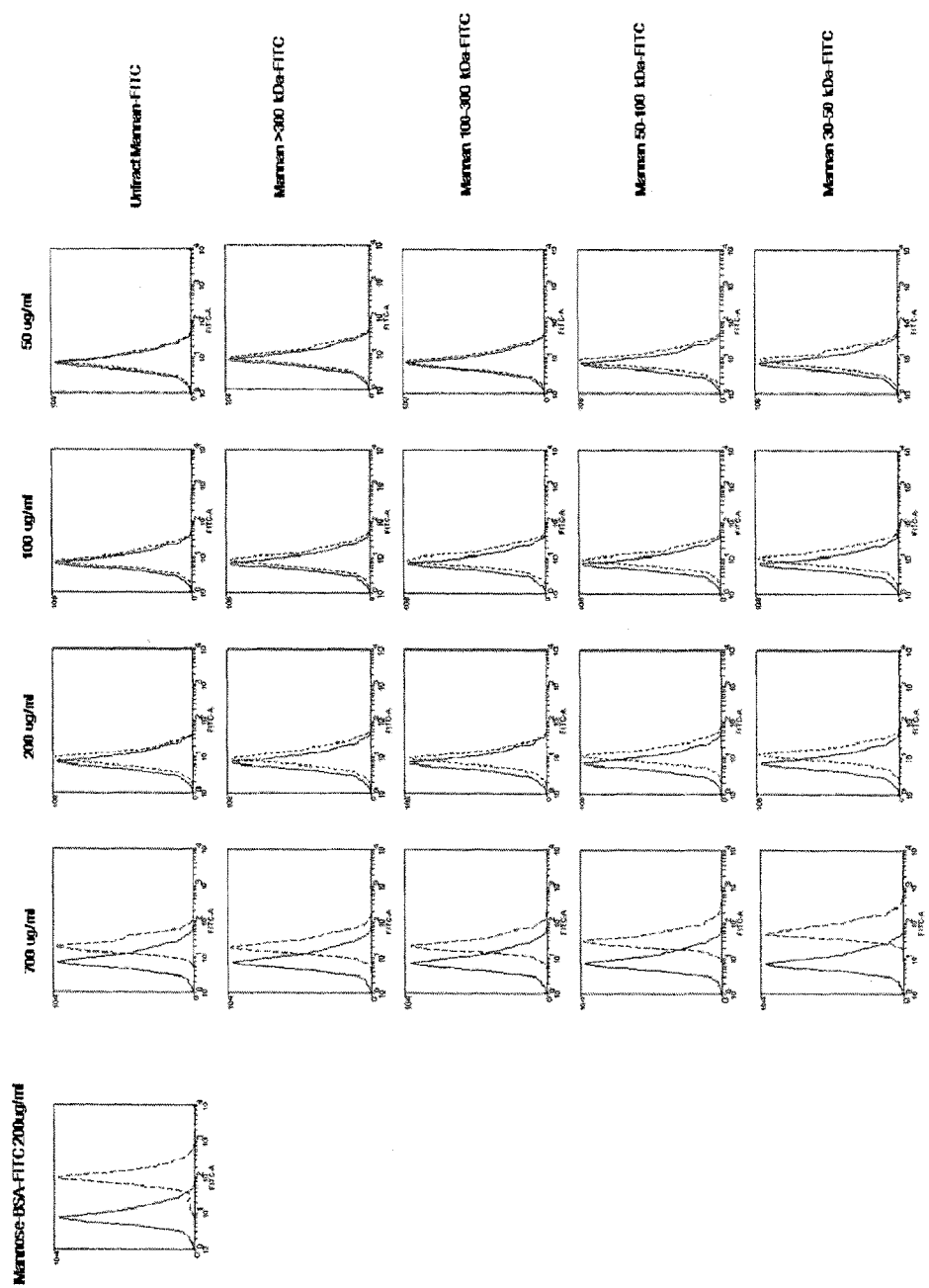

FIG. 5: Mannans were labelled with fluorocein isothiocyanate (FITC) and binding at various concentrations to huh7 human hepatoma cells was measured by flow cytometry.

Figure 6A:
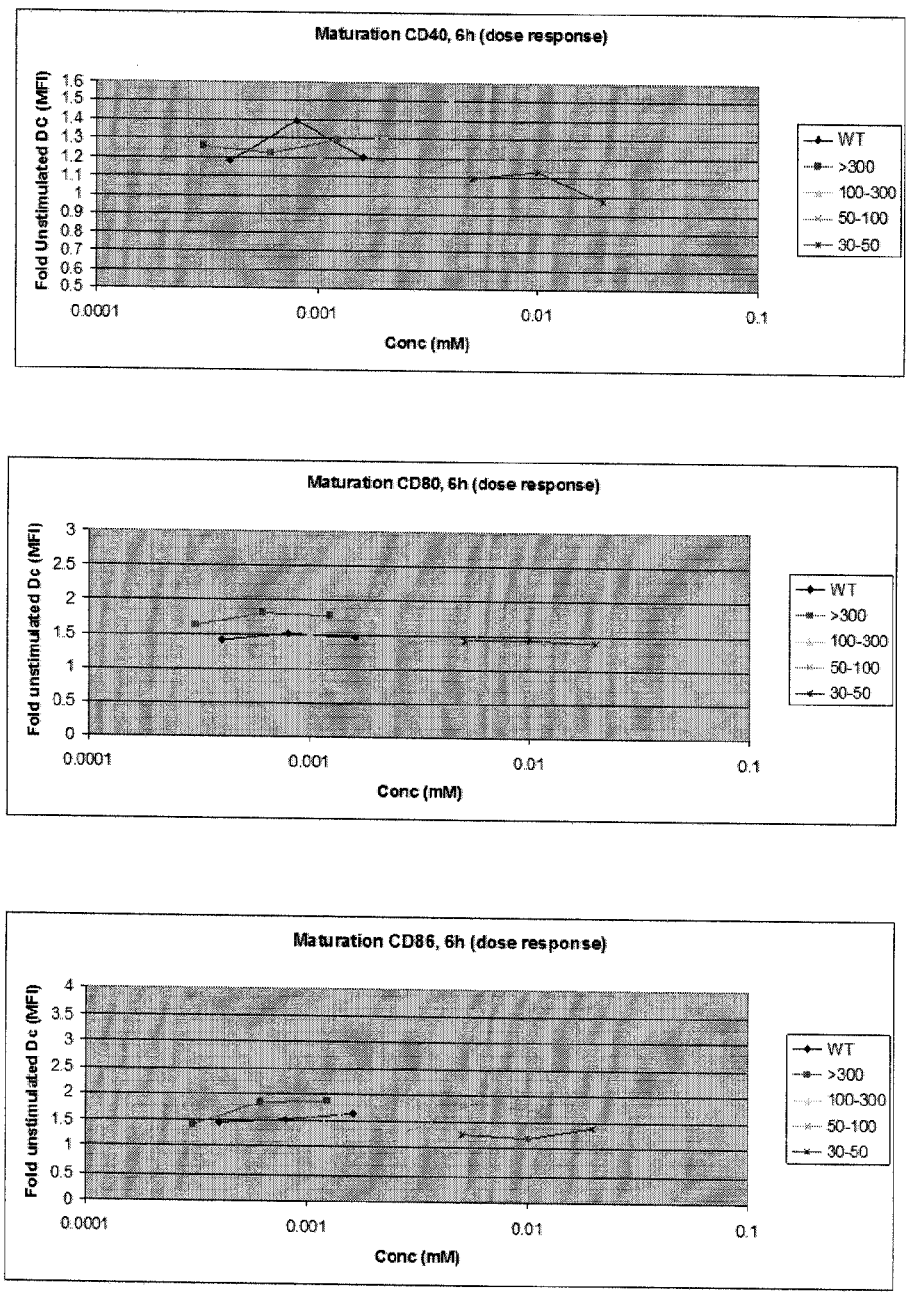
Figure 6B:
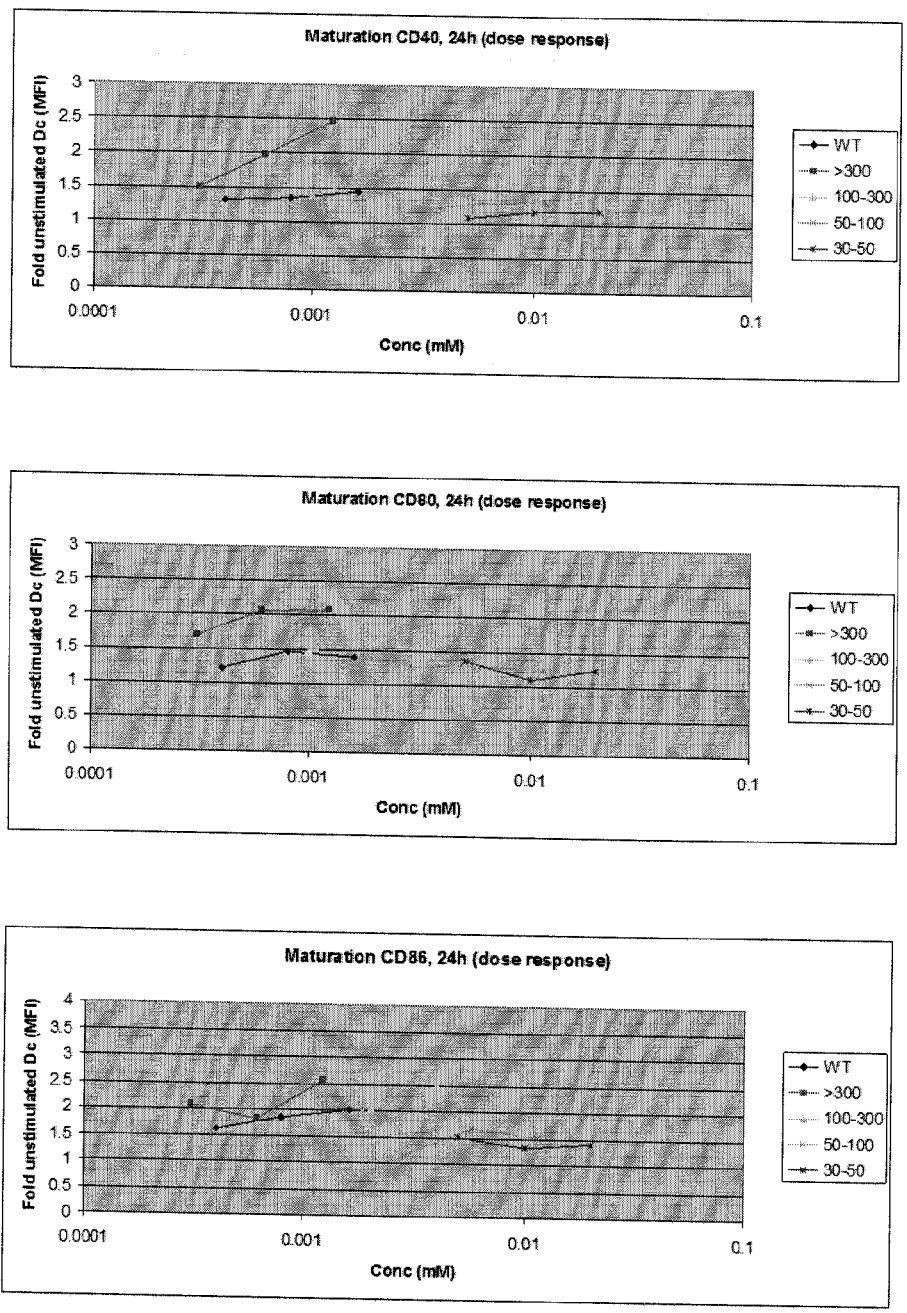
Figure 6C:
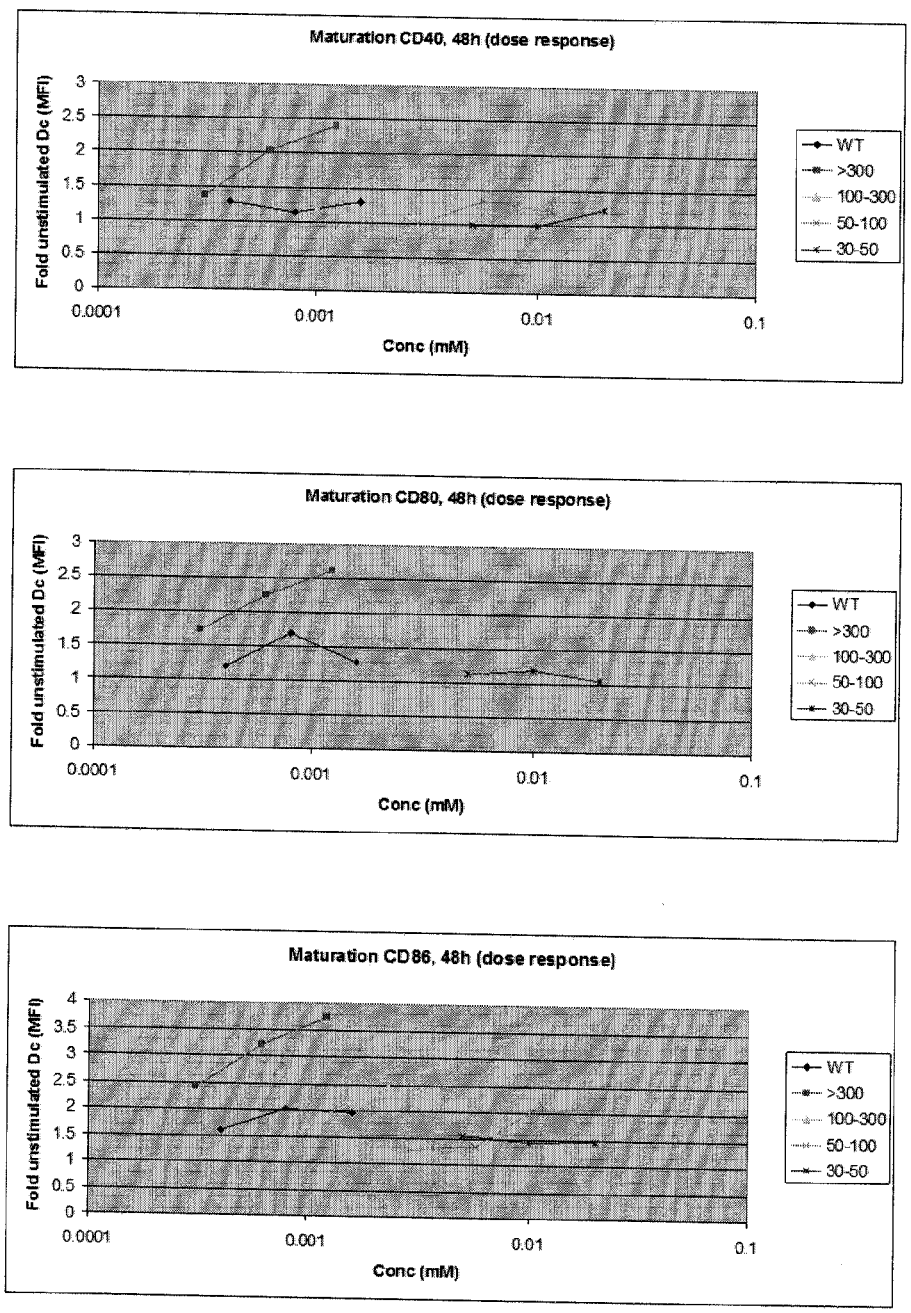

FIG. 6: Maturation of BMDCs with whole mannan and mannan fractions. The upregulation of costimulatory molecules, CD40, CD80 and CD86 was measured by flow cytometry at 6 (FIG. 6A), 24 (FIG. 6B) and 48 (FIG. 6C) hour time points. Samples were analysed at various doses.

Figure 7A:
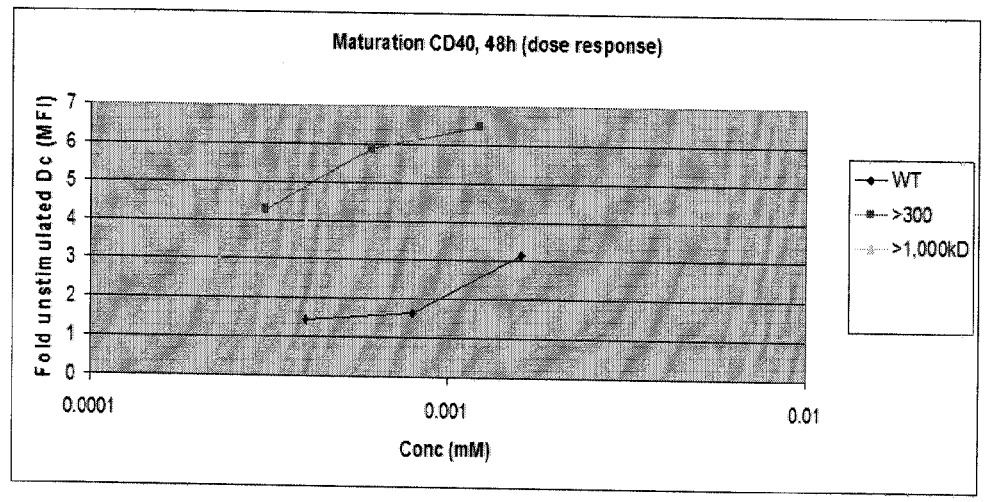
Figure 7B:
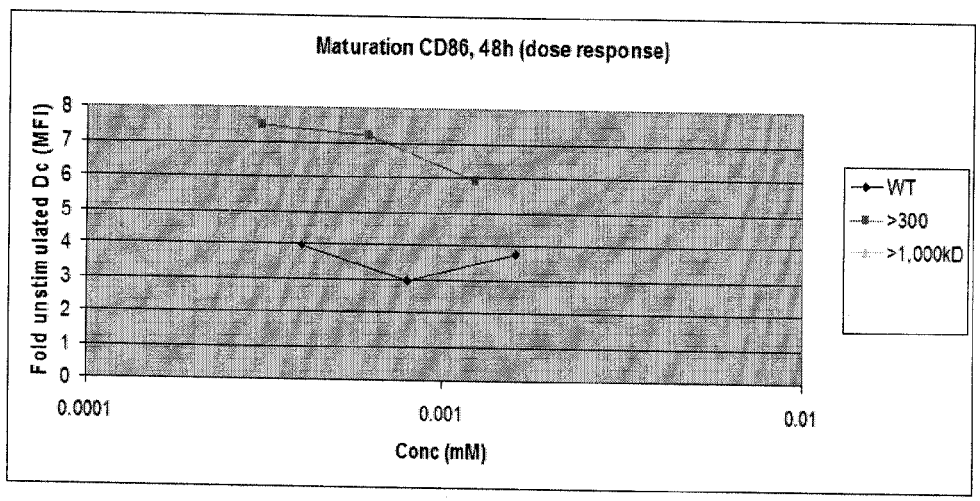

FIG. 7: Maturation of BMDCs with whole mannan, >1000 kDa mannan fraction, and >300 kDa mannan fraction. The upregulation of costimulatory molecules, CD40 (FIG. 7A) and CD86 (FIG. 7B) was measured by flow cytometry. Samples were analysed at various doses and at 48 hour time point.

Figure 8:
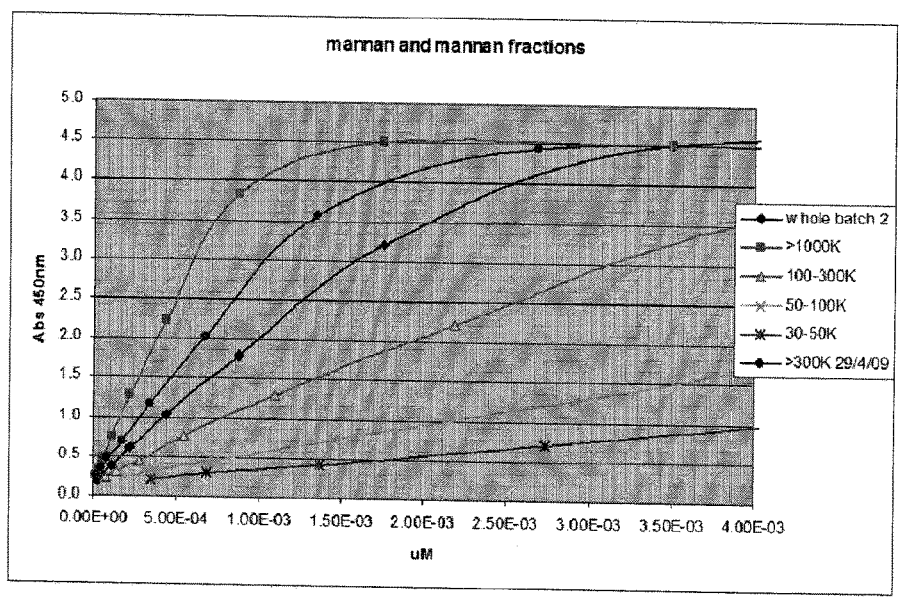

FIG. 8: Absorbance vs. concentration curve for resorcinol assay demonstrating the different mannose content of the mannan fractions.

Figure 9:
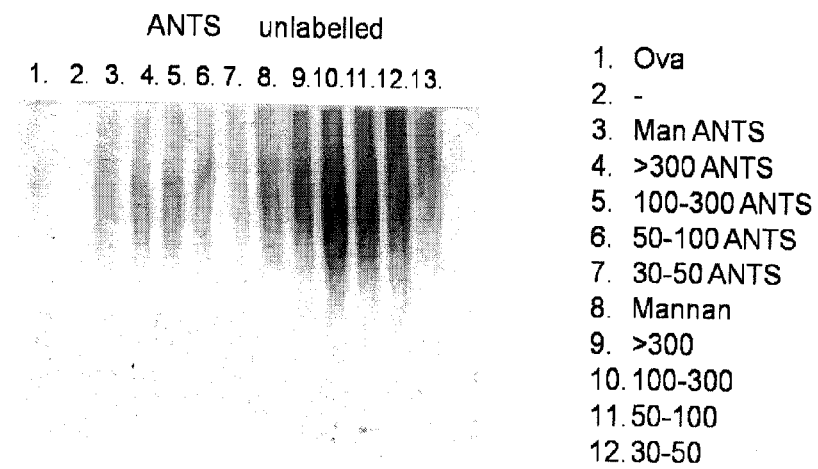

FIG. 9: Analysis of ANTS labelled mannan fractions on native PAGE gel.

Figure 10:
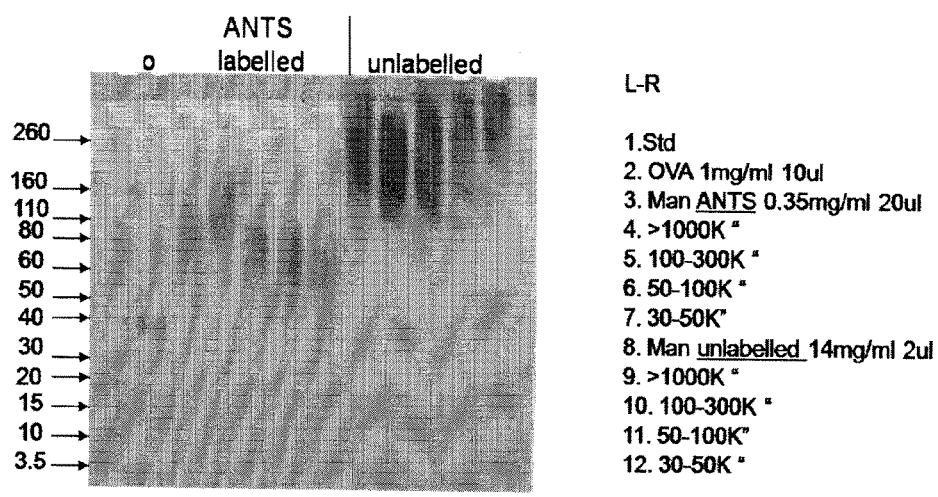

FIG. 10: Analysis of ANTS labelled mannan fractions on SDS-PAGE gel.

Figure 11A:
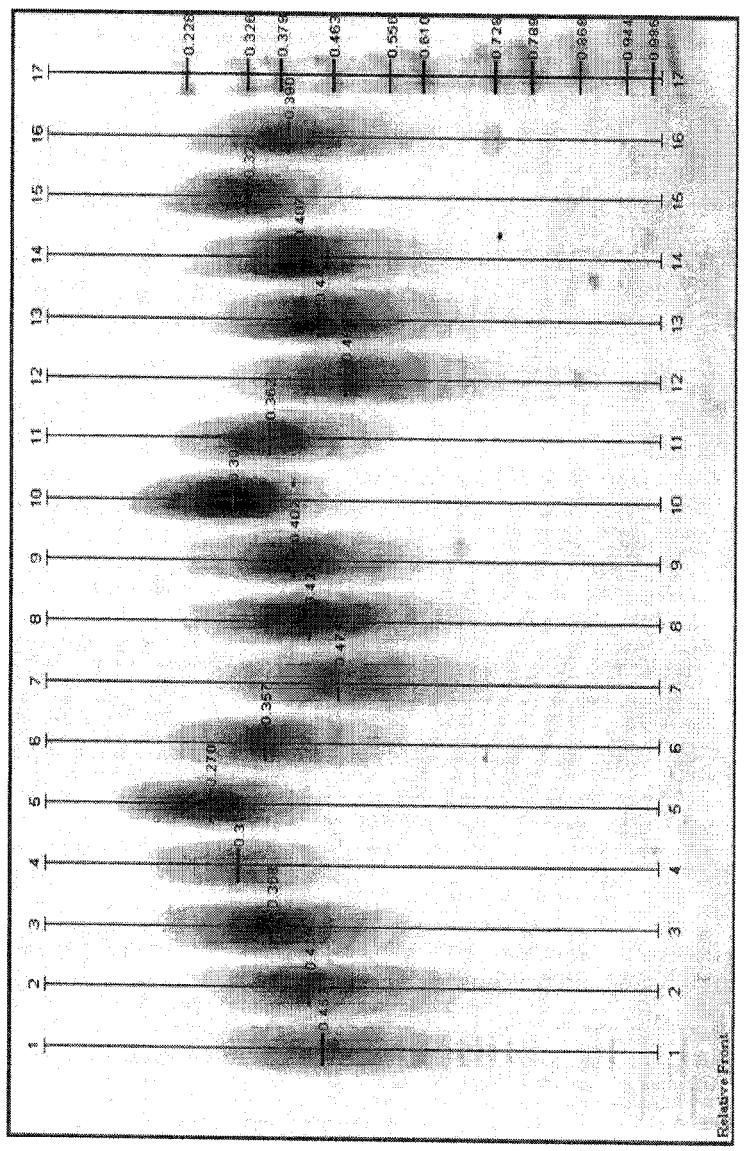
Figure 11B:
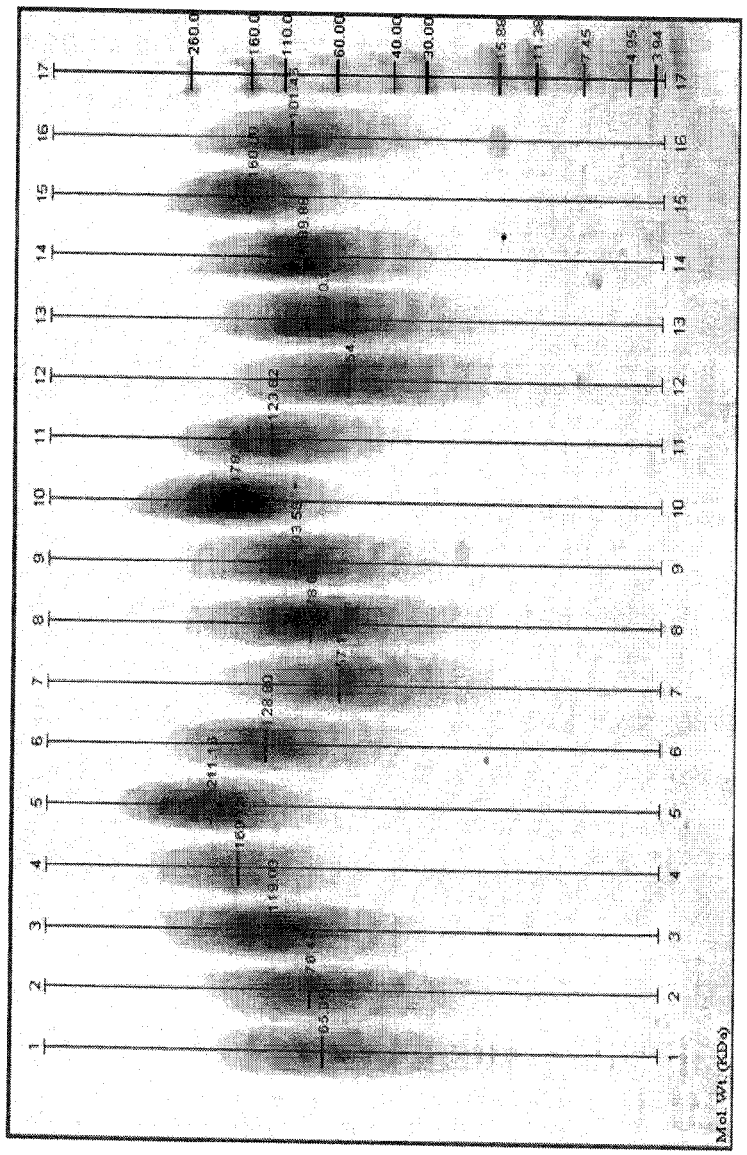

FIG. 11: Scanned SDS-PAGE gels of ANTS-labelled mannan fractions with annotated Rfs.

Figure 12:
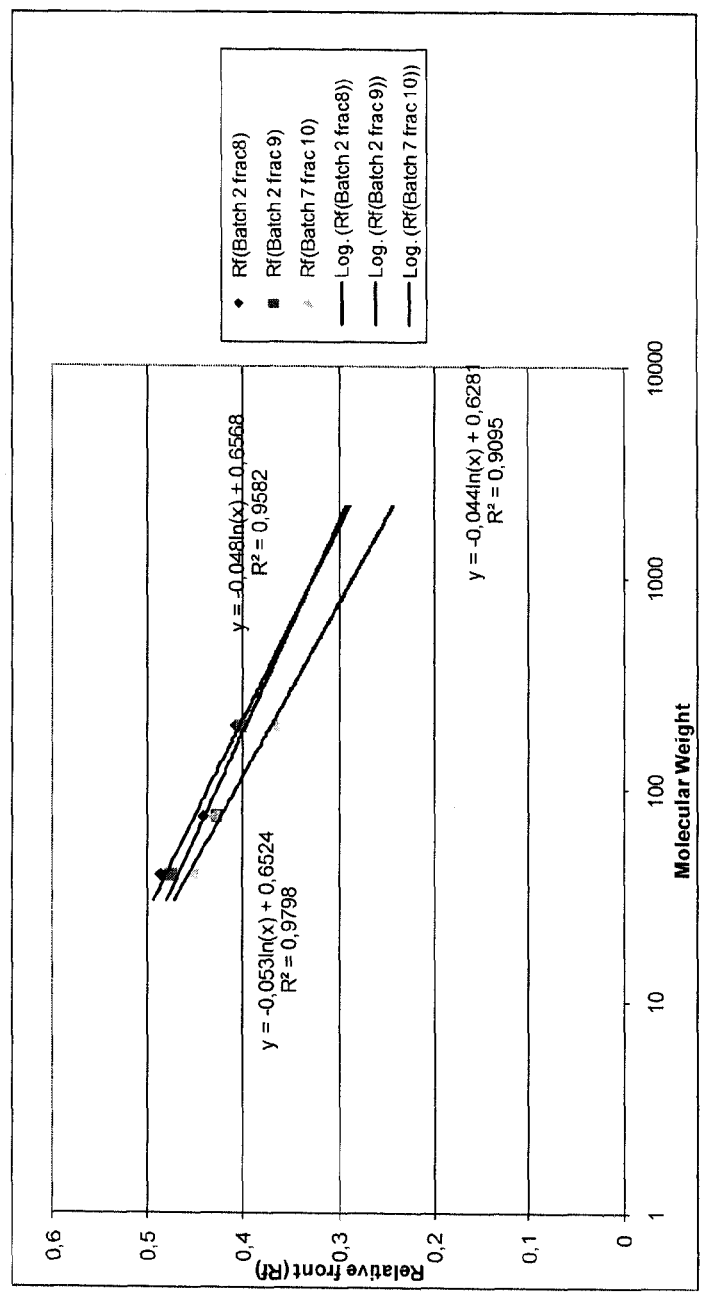

FIG. 12: Standard curves generated by Quantity one software.

Figure 13:
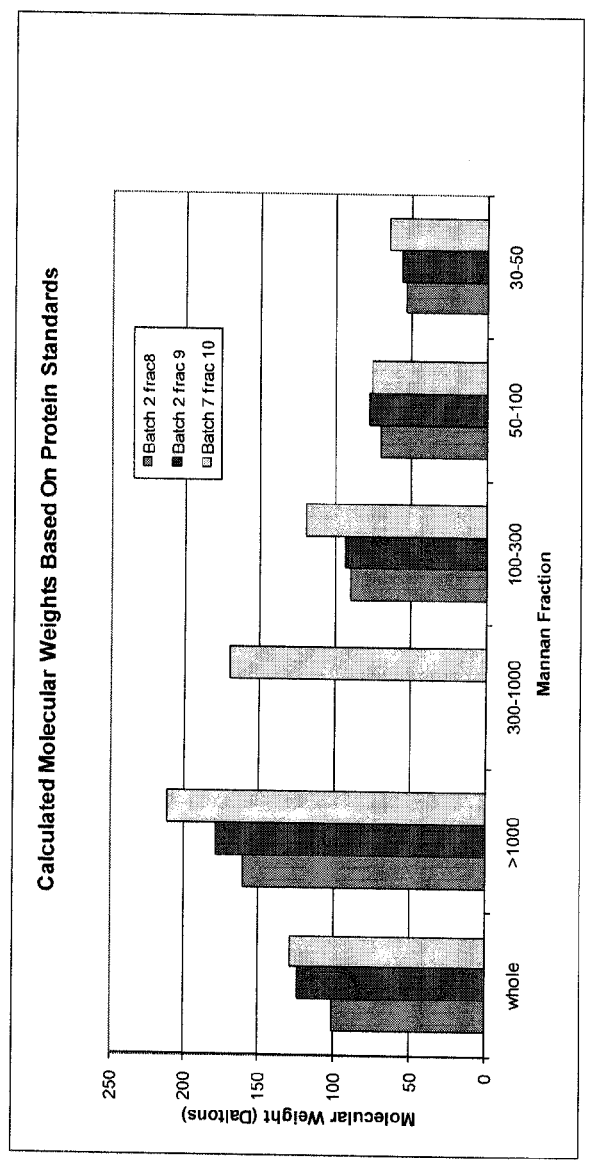

FIG. 13: Relative molecular weights based on protein standards.

Figure 14:
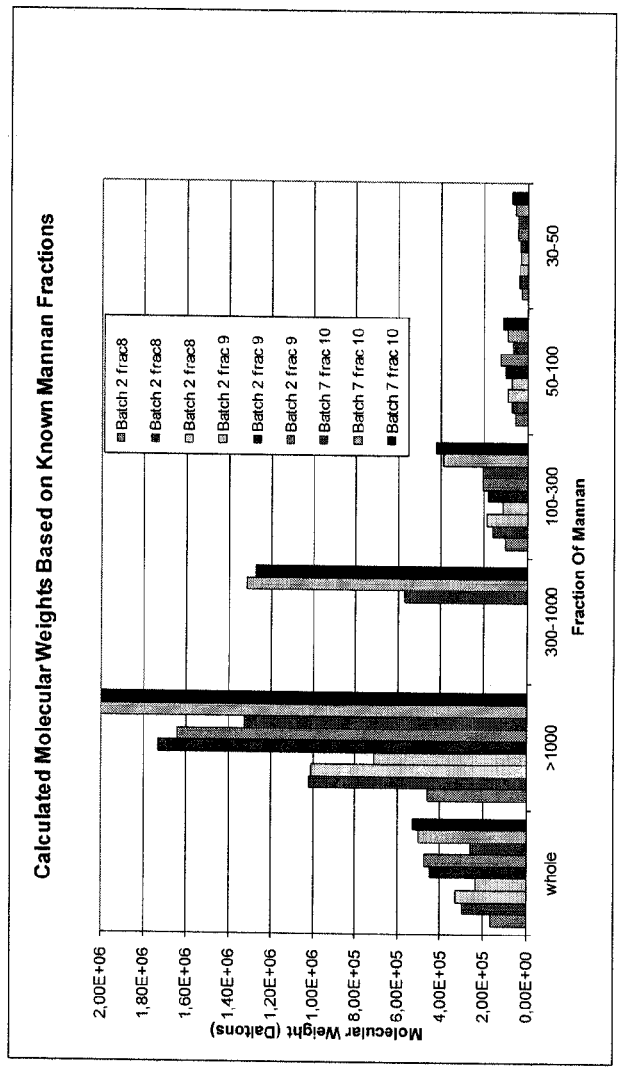

FIG. 14: Relative molecular weights based on carbohydrate standards.

Figure 15:
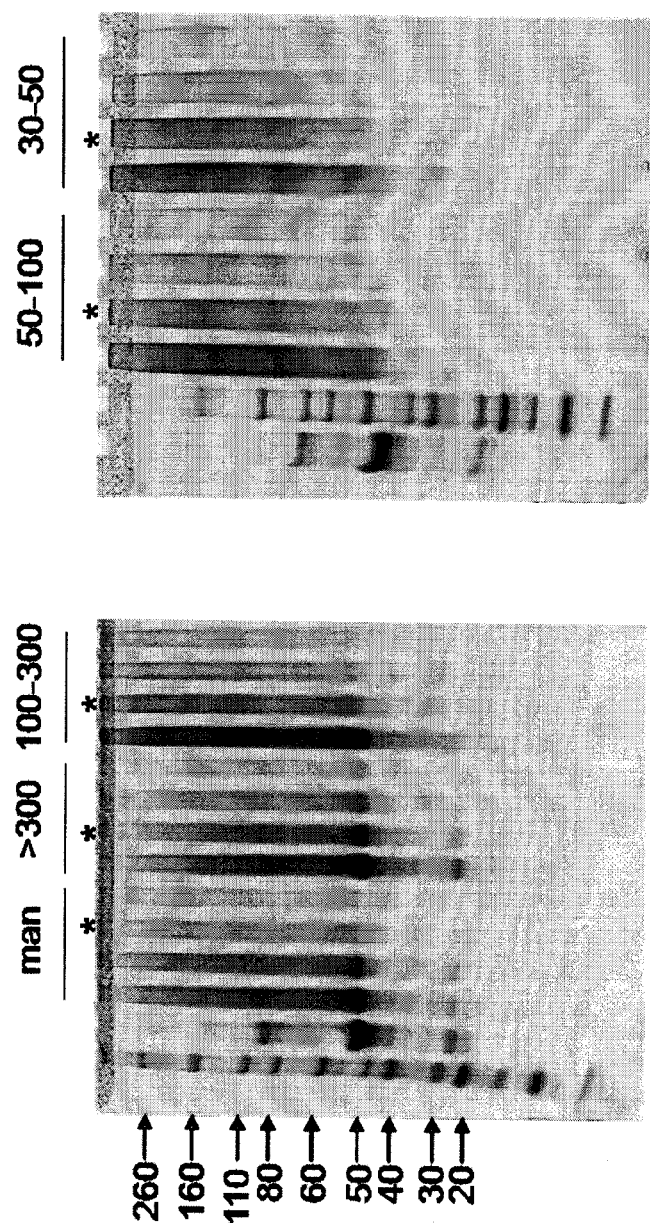

FIG. 15: Analysis of whole mannan and fractions of mannan conjugated to MUC1-FP on SDS-PAGE gels. The star denotes the conjugates incorporating the same ratio of MUC1-FP:mannan as in whole mannan-MUC1-FP conjugate.

Figure 16:
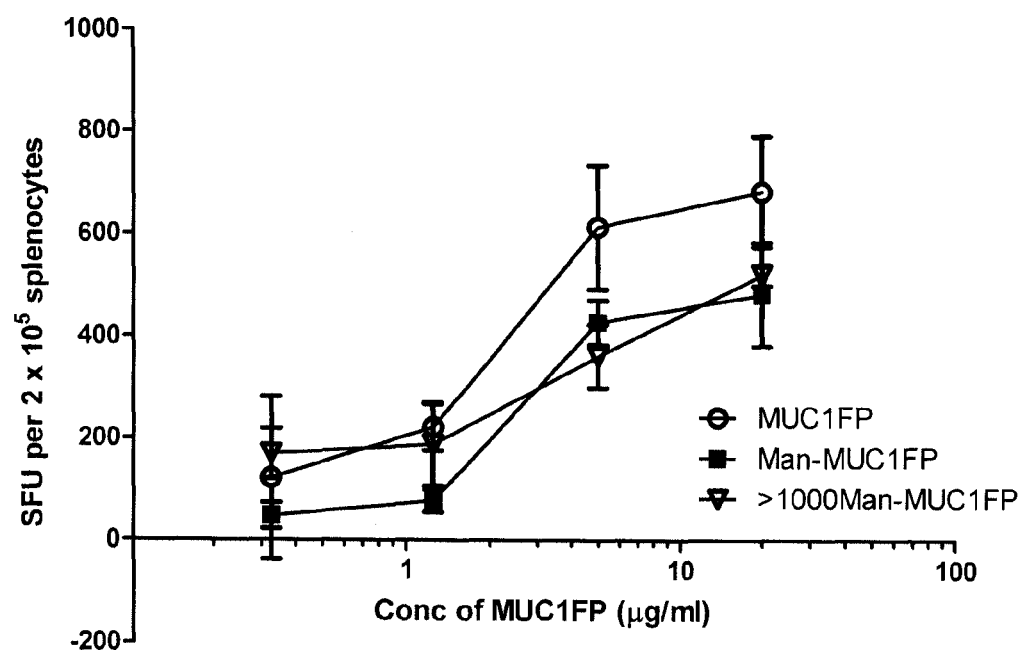

FIG. 16: MUC1-specific IFN-γ responses in splenocytes of mice immunized on day 0, 10, 17 with 10 µg of MUC1-FP, MFP or >1000 MFP.

Figure 17:
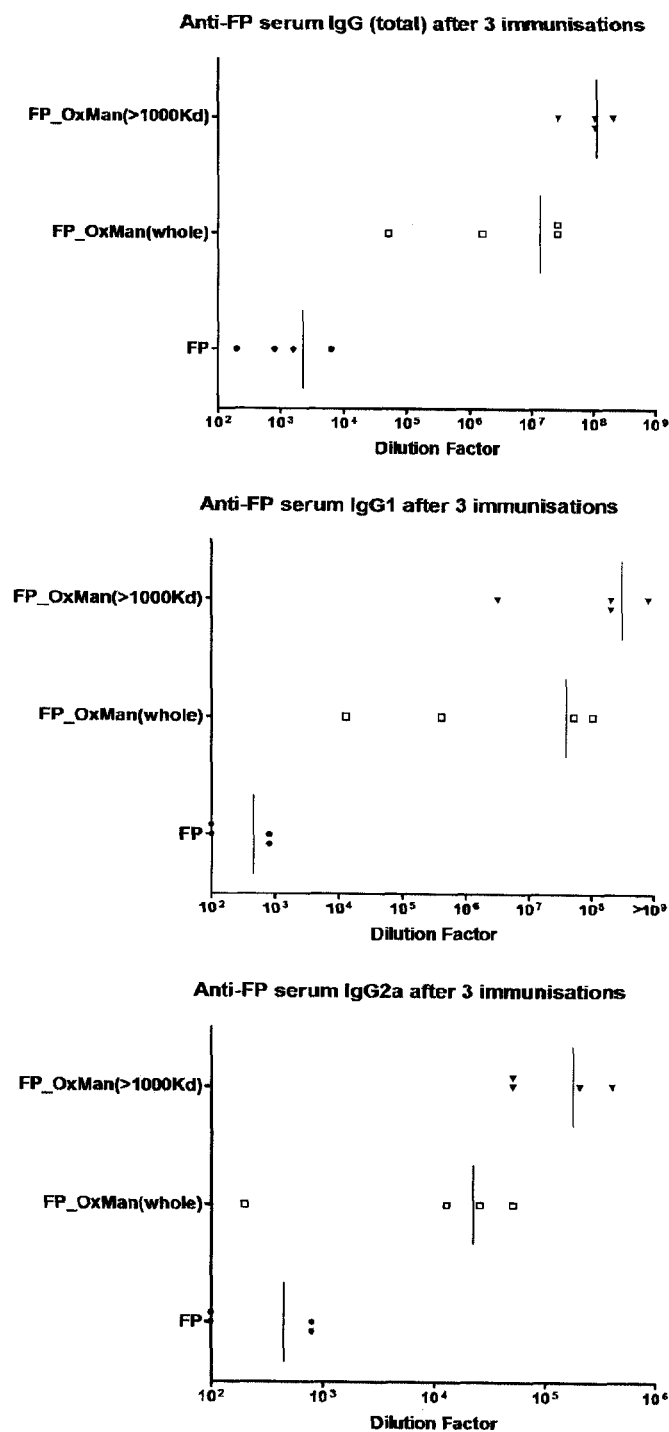

FIG. 17: Total anti-MUC1 serum IgG, IgG1 and IgG2a in mice immunized on day 0, 10, 17 with 10 µg of MUC1-FP, MFP or >1000 MFP.

FIG. 18: Mannan specifications from supplier.

Figure 19A:
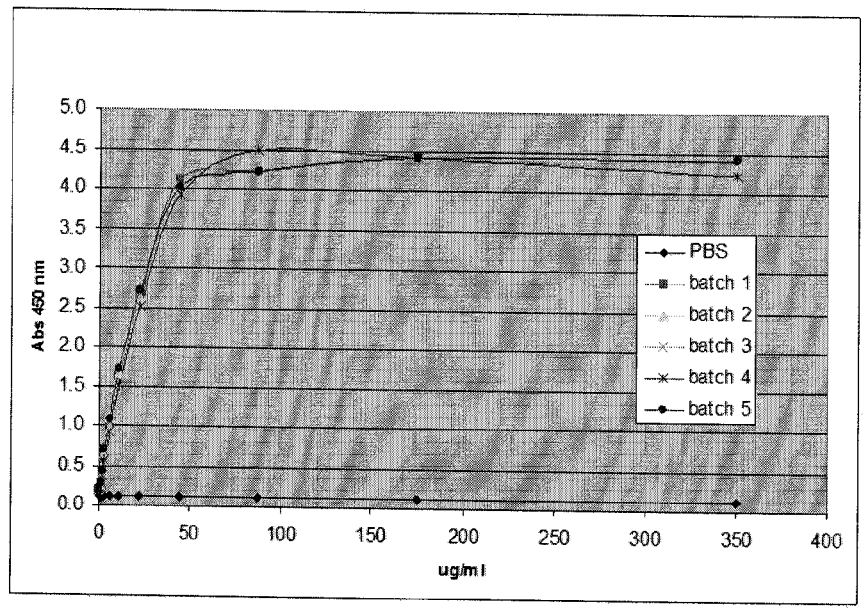

FIG. 19A: Analysis of batches of mannan using the resorcinol assay.

Figure 19B:
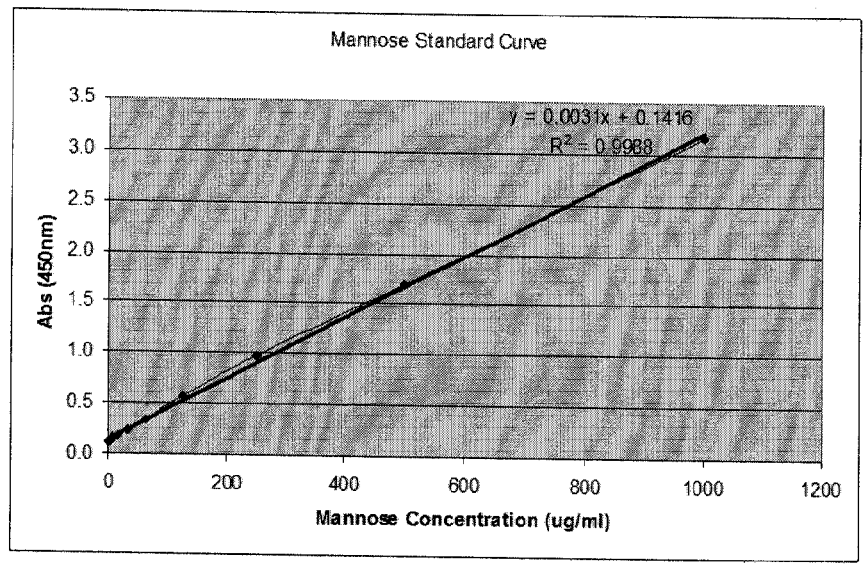

FIG. 19B: Standard curve for mannose obtained using the resorcinol assay.

FIG. 20: Comparison of various batches of mannan from Sigma by quantitating aldehyde residues after periodate oxidation.

Figure 21:
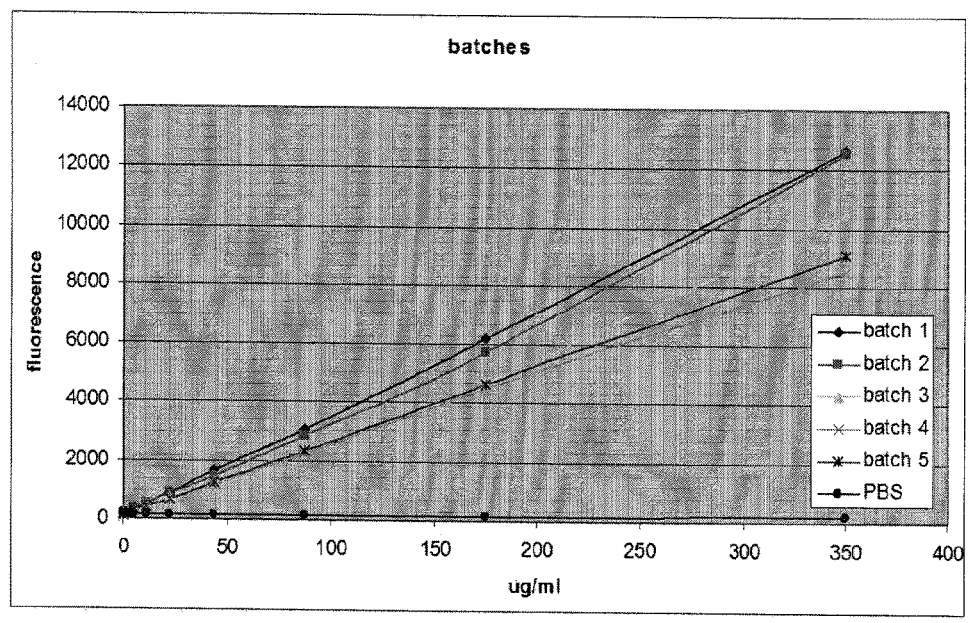

FIG. 21: Fluorescence vs. concentration curve for various batches of mannan reacted with ANTS.

Figure 22:
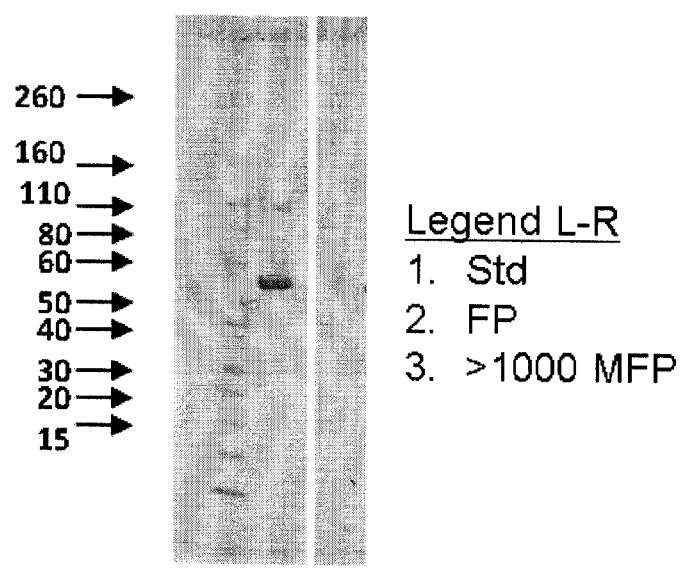

FIG. 22: Conjugation of FP to >1000 kDa oxidized mannan. Molecular weight standards, FP and >1000 MFP were run on SDS-PAGE gels (4-20%) and stained with coomassie blue.

Figure 23:
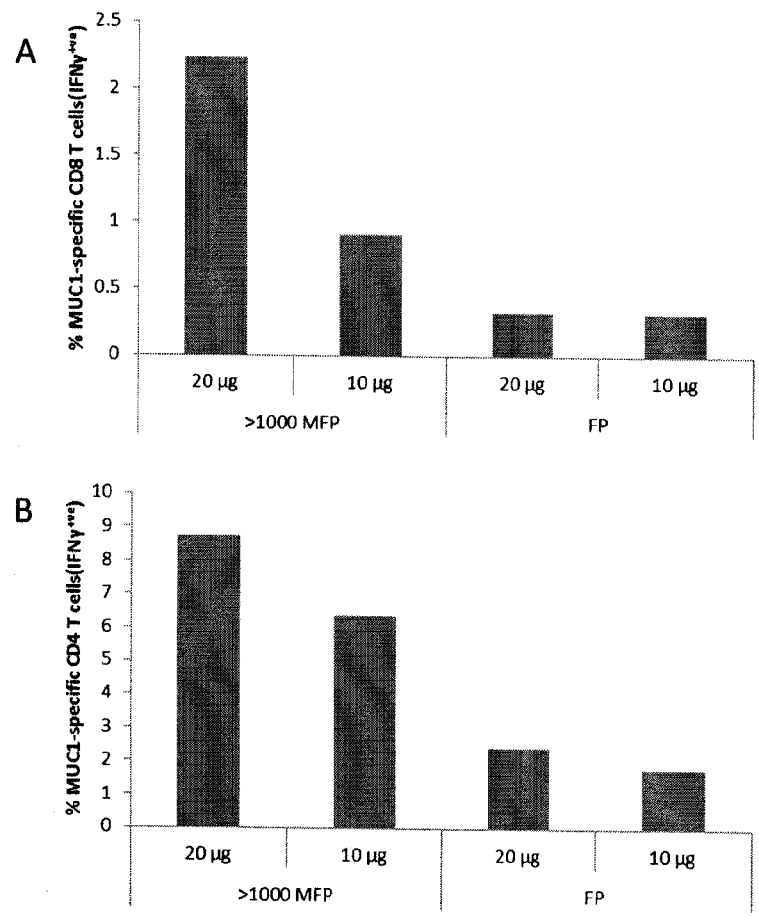

FIG. 23: Recall of MUC1-specific T cell responses. Allogeneic DCs (BC16) were pulsed with 10 and 20 µg/ml of >1000 MFP or FP and used to recall CD8 (A) and CD4 (B) intracellular IFNγ responses in a MUC1-specific T cell line.

Figure 24:
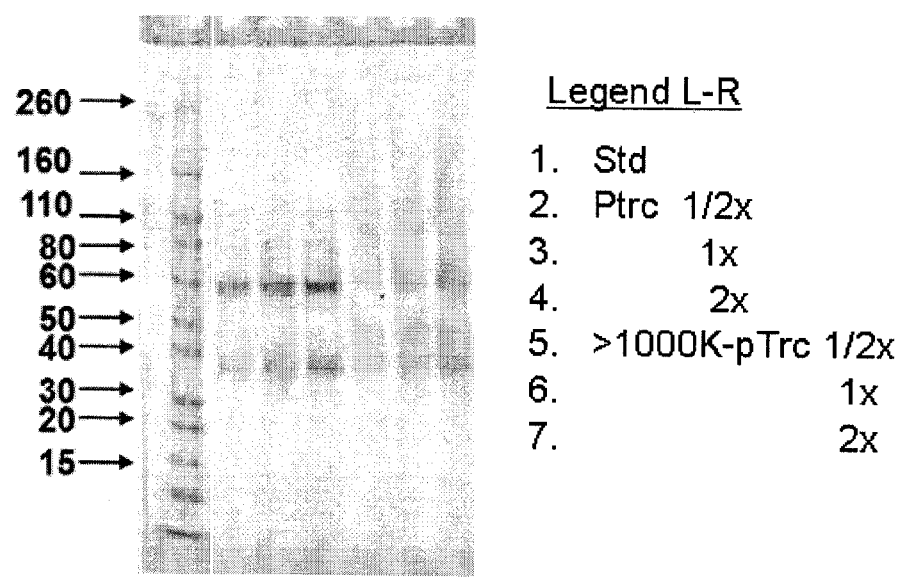

FIG. 24: Conjugation of pTrc (MUC1-VNTR) to >1000 kDa oxidized mannan. Molecular weight standards, pTrc, and >1000 kDa pTrc were run on SDS-PAGE gels (4-20%) and stained with coomassie blue.

Figure 25:
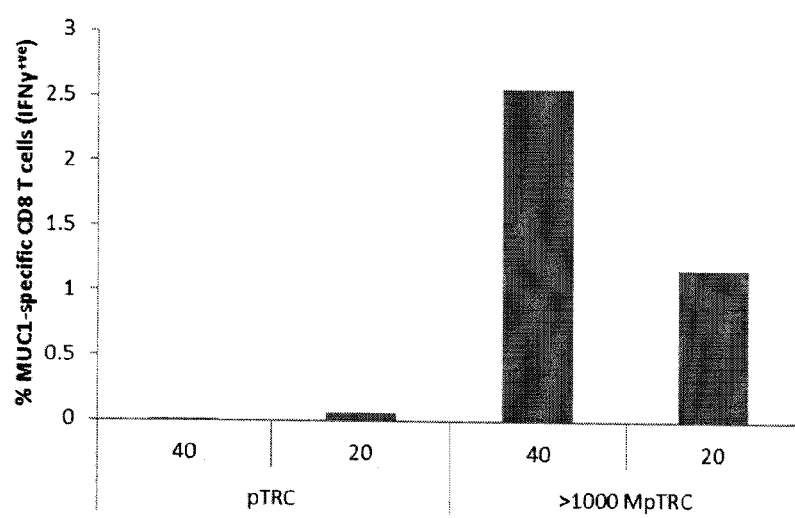

FIG. 25: Recall of MUC1-specific T cell responses. Allogeneic DCs (BC17A) were pulsed with 20 and 40 µg/ml of >1000 kDa pTrc or pTrc and used to recall CD8 intracellular IFNγ responses in a pTrc (MUC1)-specific T cell line from donor BC13.

Figure 26:
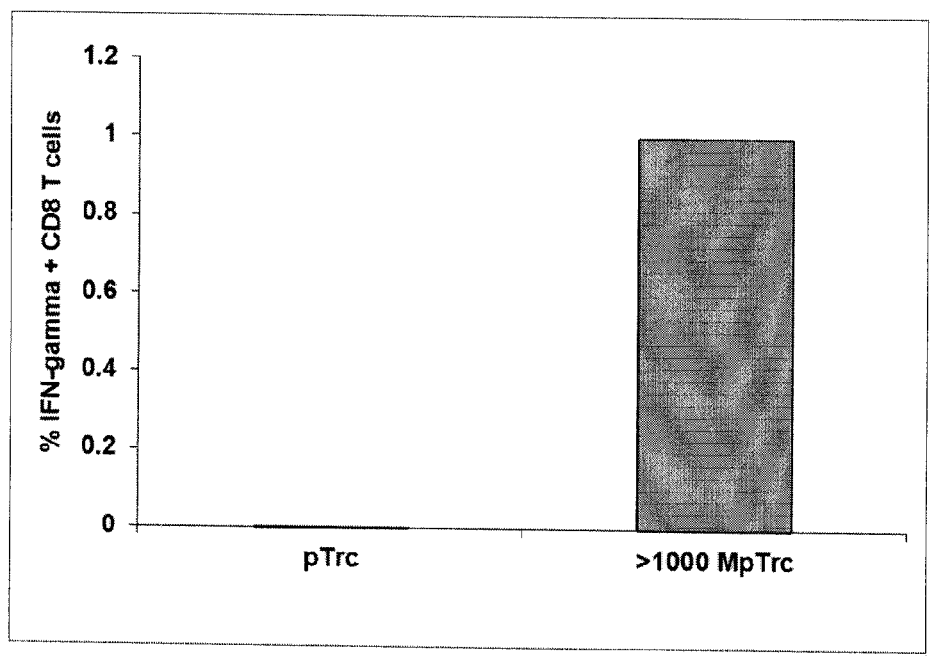

FIG. 26: Recall of MUC1-specific T cell responses. Autologous DCs were pulsed with 20 µg/ml of >1000 kDa oxidized mannan-pTrc or pTrc and used to recall CD8 intracellular IFNγ responses in a MFP-specific T cell line from donor BC17K.

Figure 27:
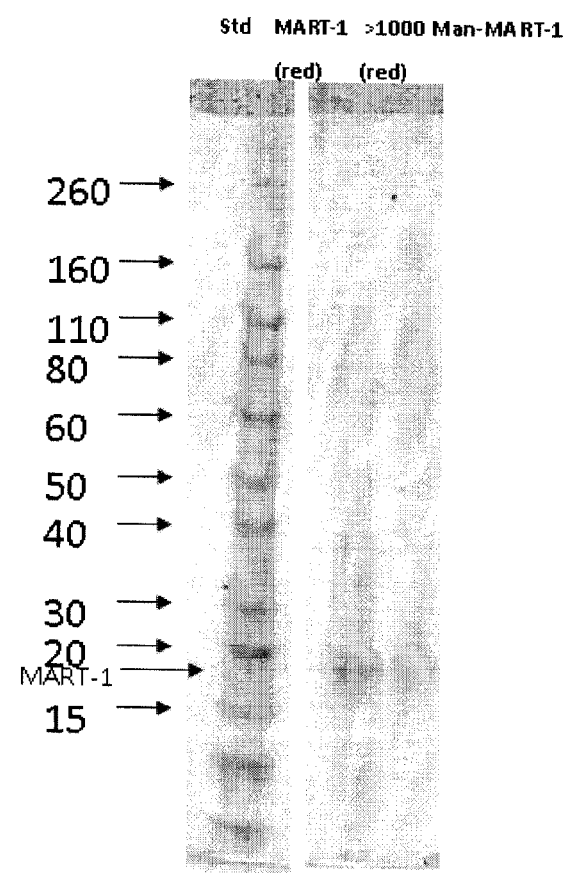

FIG. 27: Conjugation of MART-1 to >1000 kDa oxidized mannan. Molecular weight standards, MART-1, >1000 Mannan-MART-1 were run on SDS-PAGE gels (4-20%) and stained with coomassie blue.

Figure 28:
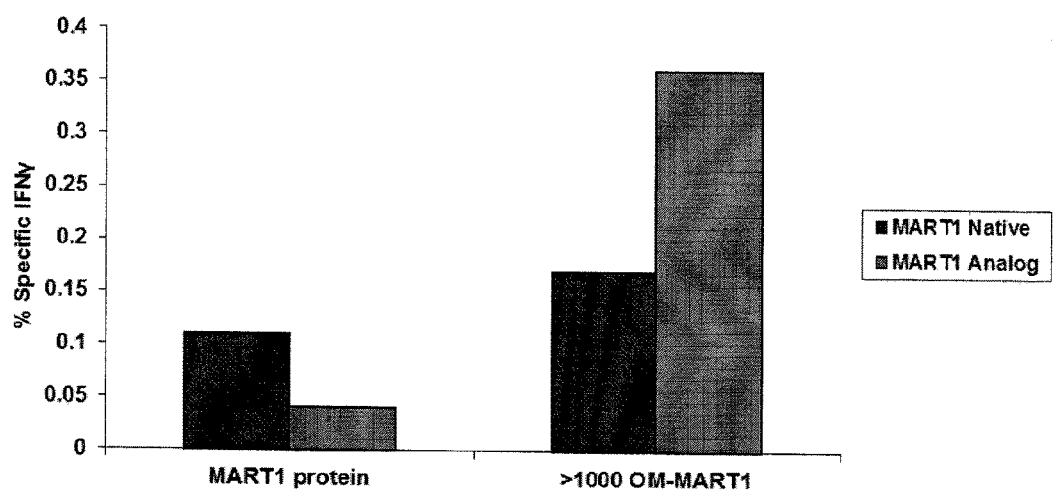

FIG. 28: Priming of MART-1-specific responses (1 stimulation). PBMCs from donor BC28 were primed with MART-1 protein or MART-1>1000 kDa oxidized mannan conjugate as described in Example 1. Recall of MART-1-specific CD8 intracellular IFNγ responses by MART-1 analog and analog peptide pulsed T2 cells are shown.

Figure 29:
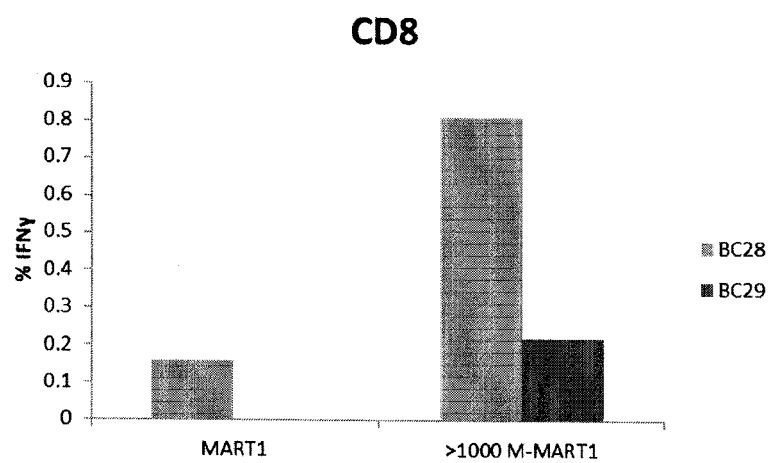

FIG. 29: Priming of MART-1-specific responses (2 stimulation). PBMCs from donor BC28 and BC29 were primed with MART-1 protein or MART-1>1000 kDa oxidized mannan conjugate as described in Example 1. Recall of MART-1-specific CD8 intracellular IFNγ responses by MART-1 protein and >1000 kDa oxidized mannan conjugate are shown.

Figure 30:
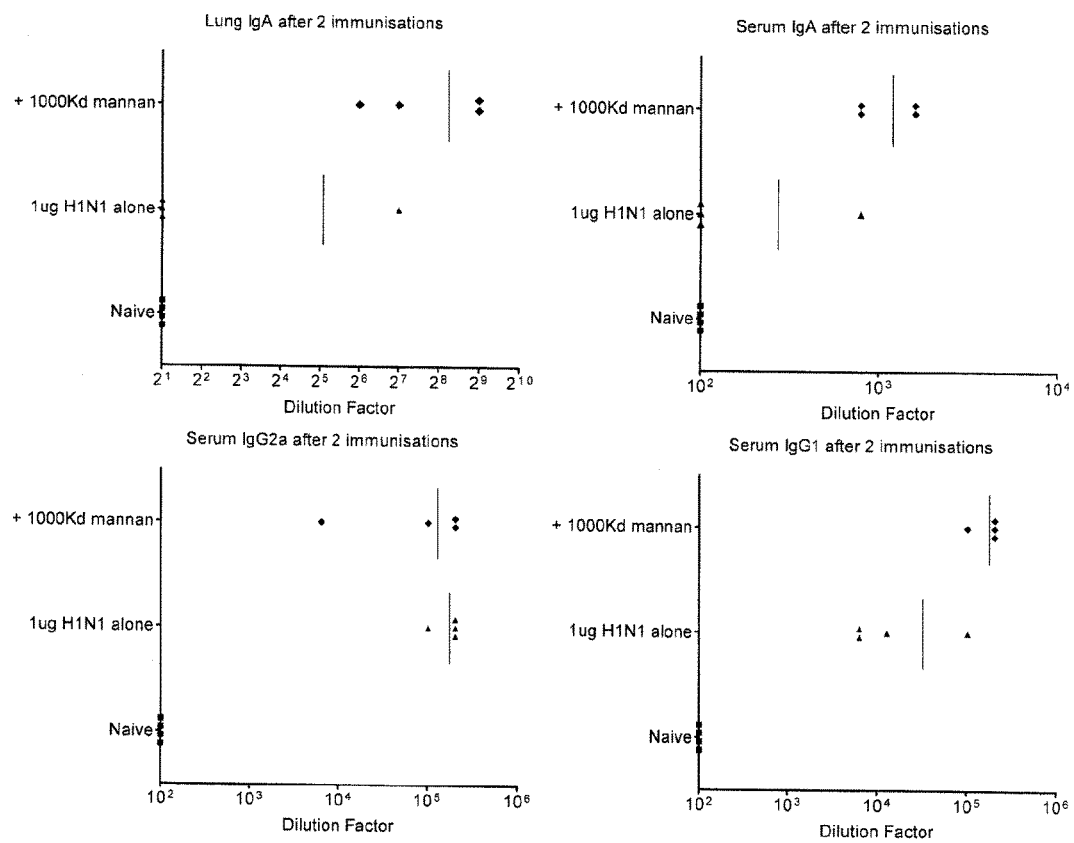

FIG. 30: H1N1-specific antibody responses to H1N1 and a mixture of H1N1+>1000 kDa mannan. Mice were immunized intranasally on days 0 and 14 with 1 µg of H1N1 either alone, or mixed with >1000 kDa mannan. Ten days after the final immunisation, serum samples and lung-wash samples were harvested and tested for anti-H1N1 IgG1, IgG2a and IgA activity by ELISA assay.

KEY TO SEQUENCE LISTING

SEQ ID NO:1: HLA-A2 epitope peptide specific for Melan/MART-1 (native)
SEQ ID NO:2: HLA-A2 epitope peptide specific for Melan/MART-1 (analog)

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, vaccine technology, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), Maniatis et al., Molecular Cloning: A Laboratory Manual, Cold Spring Harbour Laboratory Press (1982), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), F. M. Ausubel et al., (editors), Current Protocols in Molecular Biology, Greene Pub. Associates and Wiley-Interscience (1988, including all updates until present), E. Harlow and D. Lane (editors), Antibodies: A Laboratory Manual, Cold Spring Harbour Laboratory (1988), and J. E. Coligan et al. (editors), Current Protocols in Immunology, John Wiley & Sons (1991, including all updates until present).

As used herein, "about" or "approximately" shall generally mean within 20%, more preferably within 10%, and even more preferably within 5%, of a given value or range.

The term "and/or", e.g., "X and/or Y" shall be understood to mean either "X and Y" or "X or Y" and shall be taken to provide explicit support for both meanings or for either meaning.

The "subject" can be any organism whereby upon administration with a composition of the invention an immune response is induced and/or enhanced. In a preferred embodiment, the subject is an animal, more preferably a mammal or a bird. In a particularly preferred embodiment, the subject is a human. Other preferred embodiments include companion/domestic animals such as cats and dogs; livestock animals such as horses, cattle, sheep, pigs and goats, poultry, or feral animals.

Mannans and Other Carbohydrate Polymers Comprising Mannose

Surprisingly, the present inventors have found that high molecular weight mannans (i.e., greater than about 1000 kDa) have a higher immune stimulatory activity than smaller mannans or a mixture thereof. Thus, compositions of the invention comprise mannans, wherein at least 75%, more preferably at least 80%, more preferably at least 90%, more preferably at least 95%, more preferably at least 97%, more preferably at least 99%, and even more preferably all, of the mannans in the composition are greater than about 1000 kDa.

Surprisingly, the present inventors have also found that oxidized mannans having at least 150 aldehyde groups have a higher stimulatory activity than oxidized mannans comprising less than 150 aldehyde groups or a mixture thereof. Thus compositions of the invention comprise mannans, wherein at least 75%, more preferably at least 80%, more preferably at least 90%, more preferably at least 95%, more preferably at least 97%, more preferably at least 99%, and even more preferably all, of the mannans in the composition each have at least 150 aldehyde groups.

As used herein "mannans" refers to linear or branched polysaccharides formed exclusively of mannose and does not refer to polysaccharides of modified, for example, acetylated mannose (acemannans), or substituted mannans having a mannose backbone but non-mannose side groups (for example, galactomannans consisting of a mannose backbone with galactose side groups).

Mannans useful in the compositions of the invention are found in, for example, fungi, more preferably yeast. In the branched mannans from *Saccharomyces cerevisiae* (baker's yeast), the mannans consist of an α-(1→6) linked mannopyranosyl backbone structure substituted on the 0-2 atoms by side-chains of α-D-mannopyranosyl, α-D-mannopyranosyl-α-(1→2)-α-D-mannopyranosyl and α-D-mannopyranosyl α-(1→3)-α-D-mannopyranosyl-α-(1→2)-α-D-mannopyranosyl. In addition, the *S. cerevisiae* mannans can also be phosphorylated (Barreto-Bergter and Gorin, 1983; Vinogradov et al., 1998).

The mannans are preferably isolated from cell walls of fungi, more preferably, yeast. In an embodiment, the mannans may be isolated from genetically modified yeasts that have been engineered to preferentially express high molecular weight mannans, preferably mannans greater than 1000 kDa.

Mannans comprising aldehyde groups can be produced by the oxidation of mannans obtained from, for example, yeast. The most common method for introducing aldehydes into a carbohydrate polymer is by periodate-mediated (NaIO$_4$) oxidation of vicinal diols (see schematic of FIG. 2). For other methods of oxidation see generally, M. L. Wolfrom (editor), Periodate oxidation of carbohydrates, Advances in Carbohydrate Chemistry, Volume 11, pages 1-40 (1956).

In a preferred embodiment, the mannans are oxidized using NaIO$_4$ to produce polyaldehydes which are then conjugated to at least one antigen or nucleic acid encoding therefor.

In an embodiment, high molecular weight mannans (i.e., greater than about 1000 kDa) are obtained by size fractionation of whole mannan extract from, for example, yeast such as *Saccharomyces cerevisiae*. In this example, whole mannan may be derived from *S. cerevisiae* by methods known in the art, including hot water extraction of cultured cells or spray dried cells and solvent extraction methods. Mannans derived from *S. cerevisiae* may be obtained from a supplier, for example, Sigma (St. Louis, Mo.) and in an embodiment, subsequently fractionated to give a high molecular weight mannan composition.

In an embodiment, the high molecular weight mannan composition is substantially free of ribose, nucleic acids, ribonucleic acids, protein and/or other carbohydrates.

Processes of the invention relate to the preparation of compositions of the invention and more generally, compositions comprising carbohydrate polymers comprising mannose.

As used herein, a "carbohydrate polymer comprising mannose" is any multi-subunit compound comprising, more preferably consisting of, mannose subunits (i.e., mannose monomer units) or variants thereof. Examples include, but are not limited to, mannan, galactomannan and acemannan. In one embodiment, the carbohydrate polymer comprises aldehyde groups. In a preferred embodiment, the carbohydrate polymer is oxidized to a give a poly-aldehyde.

Preparation of a Carbohydrate Polymers Comprising Mannose

Methods for the separation of carbohydrates and sugars are well known in the art (see generally, Z. El Rassi (editor), Carbohydrate analysis by modern chromatography and electrophoresis, Journal of Chromatography, volume 66, Elsevier Science (2002)).

Size Fractionation

In an embodiment, size fractionation of a composition comprising a carbohydrate polymer comprising mannose, more preferably, a composition comprising mannans, is performed by tangential flow filtration (TFF), also called cross flow filtration (CFF). TFF is a process whereby product flow (feed) is directed tangentially along the surface of a membrane with most of the solution circulated back to the feed tank. The rapid flow of feed solution across the membrane acts to "sweep" the surface, reducing concentration polarization (product concentration at the membrane surface). It also prevents build-up of foulants that can plug the pores at the membrane surface. The rapid cross flow creates a pressure drop, which forces some of the feed solution and dissolved molecules that are smaller than the pores in the membrane, through the membrane filter. The solution that passes through the membrane is referred to as filtrate or permeate. Molecules or particles larger than the membrane pores are retained in the feed solution and effectively concentrated.

Membrane filtration can be classified as either a "microfiltration" or "ultrafiltration" process. Microfiltration membranes, with pore sizes typically between 0.1 micron and 1 micron, are generally used for clarification, sterilization and removal of micro-particulates or for cell harvesting. Ultrafiltration membranes, with much smaller pore sizes between 0.001 and 0.1 micron, are used for concentrating and desalting dissolved molecules (protein, peptides, nucleic acids, carbohydrates and other biomolecules), exchanging buffers, fractionation and water purification. Ultrafiltration membranes are typically classified by molecular weight cut off (MWCO), rather than pore size.

In another embodiment, size fractionation of a composition comprising a carbohydrate polymer comprising mannose is performed by size exclusion chromatography.

The basic principles of size exclusion chromatography are well known to those in the art, and are explained in "Gel filtration: Principles and Methods, GE Healthcare". The appropriate columns for fractionating particular ranges can be readily selected and effectively used to resolve the above fractions, for example, Sephacryl S-100 HR, Sephacryl S-200 HR, Sephacryl S-300 HR, Sephacryl S-400 HR and Sephacryl S-500 HR or their equivalents. In an analogous fashion, Sepharose media or their equivalents, for example, Sepharose 6B, 4B, 2B, could be used. In an embodiment, Sephacryl S-400 HR is used to fractionate the composition comprising the carbohydrate polymer comprising mannose.

In yet another embodiment, size fractionation of a composition comprising a carbohydrate polymer comprising mannose is performed by ultrafiltration.

Ultrafiltration of the sample could be performed using molecular membranes with appropriate molecular mass cut-offs. The specific membranes and procedures used to effect fractionation are widely available to those skilled in the art.

Those skilled in the art will also appreciate that the size fractionation of a composition comprising a carbohydrate polymer comprising mannose may also be performed by density gradient centrifugation.

In preferred embodiments, the sample is at least partially purified before fractionation to remove contaminants, such as, for example, ribose, nucleic acids including DNA and RNA, protein and/or carbohydrates not comprising mannose. Purification could be achieved in combination with other chromatography techniques, including affinity, ion exchange, and hydrophobic interaction chromatography. The purity of a composition could be determined by measuring its mannose content as described below.

One method of removal of non-carbohydrate components is the use of digestion enzymes to cleave the non-carbohydrate components, followed by size fractionation to remove the cleaved products. Digestion enzymes including pronase, ribonuclease, DNase and proteases, are well known in the art and described in various text books, one example of which is Maniatis et al. (1982), supra. Proteases useful for digestion of proteins include endo- and exopeptidases, pronase, serine proteases such as trypsin, chymotrypsin and subtilisin, thiol proteases such as papain, and calcium-requiring proteases such as thermolysin.

Alternatively, non-carbohydrate components may be removed by affinity chromatography, for example by use of DNA- or RNA-binding matrices (Maniatis et al., 1982, supra). Another option is to purify the carbohydrate polymer away from the contaminating components by use of polysaccharide binding matrices such as lectins.

According to the processes of the invention, the size distribution, aldehyde and/or mannose content of the carbohydrate polymer comprising mannose in a selected fraction can be determined. This validation may be important in gaining regulatory approval for use in humans.

Size Distribution

The size distribution of a sample prior to and/or following fractionation can be determined. When carried out prior to fractionation, this analysis aids in the selection of a starting composition of the carbohydrate polymer for fractionation. For example, if a majority of the molecular weight species of the polymer in the starting composition is below 1000 kDa, the composition can be discarded and another batch having a higher distribution of high molecular weight species of the carbohydrate polymer selected for fractionation. In contrast, analysis of the size distribution of the recovered fraction acts to confirm or validate the fractionation process. This will be important when gaining regulatory approval for use of these carbohydrate polymers in humans.

The size distribution of the carbohydrate polymers of a composition may be determined by reacting an oxidized sample with ANTS (see schematic of FIG. 3), and resolving the ANTS labelled sample by SDS-PAGE. Comparison of the resolved ANTS labelled sample against protein and/or carbohydrate standards will allow for the size distribution of said sample to be determined.

As used herein "protein and/or carbohydrate standards" refers to a composition of known proteins or carbohydrates of various molecular weights for use as molecular weight standards in SDS-PAGE. The composition is designed to give sharp, well-separated bands that serve as markers for estimating the molecular weight of samples electrophoresed in neighbouring lanes of the same gel. The standards may be prestained (to allow for easy visualization of molecular weight ranges during electrophoresis) or unstained. A variety of standards are available for electrophoresis applications and can be purchased from, for example, Invitrogen or Bio-rad. Typically, the standards are supplied in ready-to-use format, eliminating the need to reduce, pre-mix or add loading dyes. These standards are consistent from lot to lot and strictly quality controlled on appropriate gels to ensure consistent band migration and intensity.

Aldehyde Content

The aldehyde content of a sample may also be determined prior to and/or after fractionation to aid in batch selection and/or fraction validation.

In an embodiment, the aldehyde content of a sample is determined by quantitating the number of aldehyde residues in the sample following oxidation with $NaIO_4$. For example, a composition comprising mannans may be selected for fractionation if the mannans each comprise approximately 90-200 aldehyde residues.

The method involves first oxidizing the sample by for example, reacting 1.4 mg sample in 100 μl in 0.1 M phosphate buffer pH 6.0 with 0.01 M $NaIO_4$ for 1 hour on ice in the dark. The reaction is then quenched with 10 μl ethanediol and allowed to react for a further ½ hour before being loaded on a PD10 column pre-equilibrated with 0.1 M acetate buffer pH 4.8 to remove excess $NaIO_4$.

The number of aldehyde groups can subsequently be measured by spectrophotometry by measuring the release of pyridine-2-thione when treated with PDPH.

As understood by those skilled in the art, several other methods may be used for the quantitation of aldehydes. For example, oximes, hydrazides, semicarbazide, and carbohydrazides readily react with aldehydes and can be attached to reporter molecules (e.g., fluorescent compounds) for the quantitation of aldehyde groups in the carbohydrate polymer. A selection of fluorescent compounds that can be used is detailed in www.invitrogen.com/site/us/en/home/References/Molecular-Probes-The-Handbook/Reagents-for-Modifying-Groups-Other-Than-Thiols-or-Amines/Hydrazines-Hydroxylamines-and-Aromatic-Amines-for-Modifying-Aldehydes-and-Ketones.html. Examples include fluorescein-5-thiosemicarbazide, Alexa Fluor 488, Alexa Fluor 555, Alexa Fluor 568, Alexa Fluor 594, Alexa Fluor 633, Alexa Fluor 647 and Texas Red.

In addition, 2,4-dinitrophenylhydrazine reacts with aldehydes to form a red hydrazone which can also be used to quantitate the number of aldehyde groups in the carbohydrate polymer by absorbance spectrophotometry (Apostolopoulos et al., 2000).

Mannose Content

In an embodiment the mannose content of the composition is determined by a colorimetric assay for neutral sugars, in which neutral sugars react with resorcinol in the presence of a hydrated sulphuric acid solution.

For example, 200 μl of 6 mg/ml resorcinol and 1 ml 75% sulphuric acid is added to an assay tube containing a sample (dissolved in 0.01 M acetic acid) having 5 to 100 nmol of neutral sugars in a volume of 200 μl. The solutions are then vortexted and heated at 90° C. in a temperature-regulated water bath for 30 minutes and subsequently placed in a cold-water bath for 30 minutes in the dark. The optical density of the mixture is then determined at 430 or 480 nm. The same assay can be conducted by using the half volumes indicated above with similar results.

Alternatively, the assay can be conducted in microplate format. In this embodiment, 20 μl of 6 mg/ml resorcinol and 100 μl 75% sulphuric acid and 50 μl pristine is added to a U-shaped well of a 96-well microtiter plate containing a sample (dissolved in 0.01 M acetic acid) having 1 to 100 nmol of neutral sugars in a volume of 20 μl. The solutions are then mixed by shaking the plate with a vortex apparatus and heated at 90° C. in an incubator for 30 minutes and subsequently kept at room temperature for 30 minutes in the dark. The optical density of the mixture is then determined at 430 or 480 nm using a microtiter plate reader. For quantitative purposes, blanks, neutral sugar standards, and samples are assayed in duplicate, more preferably, triplicate, more preferably, quadruplicate.

The mannose content can also be determined by enzymatic or acid hydrolysis of the carbohydrate polymers followed by analysis by HPLC, mass spectrometry, capillary electrophoresis or thin layer chromatography (Wang et al., 2007; Anumula, 1994; R. Townsend, Chromatography in Biotechnology, C. Horvath and L. S. Ettre (editors), American Chemical Society, Washington, D.C. (1993) pp. 86-101).

Immunostimulatory and Vaccine Compositions

As used herein, the term "immunostimulatory composition" refers to the capability of the composition to induce and/or enhance an immune response.

The term "immune response" has its ordinary meaning in the art, and includes both humoral and cellular immunity. An immune response can manifest as one or more of, the development of anti-antigen antibodies, expansion of antigen-specific T cells, increase in tumor infiltrating-lymphocytes (TILs); development of an anti-tumor or anti-tumor antigen delayed-type hypersensitivity (DTH) response, clearance of the pathogen, suppression of pathogen and/or tumor growth and/or spread, tumor reduction, reduction or elimination of metastases, increased time to relapse, increased time of pathogen or tumor free survival, and increased time of survival. An immune response may be mediated by one or more of, B-cell activation, T-cell activation, natural killer cell activation, activation of antigen presenting cells (e.g., B cells, DCs, monocytes and/or macrophages), cytokine production, chemokine production, specific cell surface marker expression, in particular, expression of co-stimulatory molecules. The immune response may be characterized by a humoral, cellular, Th1 or Th2 response, or combinations thereof.

Humoral Response

In an embodiment, administration of the composition or vaccine results in a humoral response, wherein one or more of IgA, IgG, IgM and optionally, IgE antibody production is stimulated.

The immunoglobulins may include one or more of the subclasses within each class of antibody, for instance IgG2a and IgG1.

In one embodiment, IgG1 and/or IgA production is stimulated.

In some instances, stimulation of IgE production may be beneficial, for example, to immunize against worm infections.

In other instances, a reduction in total IgE production, or a reduction in the level of IgE relative to other antibody classes, can be beneficial, for example, to prevent or reduce type I hypersensitivity or atopy, for example, hayfever, asthma attacks or food and other allergies. IgE binding to its receptor and subsequent cross-linking with allergen is responsible for triggering immune responses underlying conditions such as asthma including atopic asthma, allergic rhinitis and atopic dermatitis, which are health problems of epidemic proportions. Thus, in an embodiment, the immune response is such that IgE production is reduced.

In another embodiment, the IgE titre relative to one or more of IgA, IgG, IgM or subclasses of these is reduced. IgE production may be unchanged, whilst the production of one or more of the other antibodies is increased upon immunization with the composition.

In an embodiment, the immunization selectively stimulates production of one or more of IgA, IgG and IgM over IgE.

In an embodiment, IgA production is stimulated, and the titre of IgA at one or more mucosal areas, and/or in the serum, is increased.

In an embodiment, IgA production upon immunization is greater when compared with production of IgG, IgM and IgE.

In another embodiment, immunization results in greater production of IgA relative to the increase in IgG1 and/or IgG2a production.

In yet another embodiment, IgG production is stimulated, and the titre of IgG at one or more systemic areas and/or in the serum, is increased.

In an embodiment, IgG production upon immunization is greater when compared with production of IgA, IgM and IgE.

In another embodiment, immunization results in greater production of IgG relative to the increase in IgA.

In an embodiment, immunization results in greater production of IgG2a relative to the increase in IgG1.

Cellular Immune Response

In an embodiment, administration of the composition or vaccine of the invention results in a cellular response, wherein one or more antigen presenting cells are activated.

In an embodiment, macrophages and/or DCs are activated.

Activation of DCs may result in elevated surface expression of co-stimulatory molecules including, for example, CD40, CD80 and 86 and/or an increase in pro-inflammatory cytokines, for example, IL-12 and/or IL-4 and/or an increase in MHC class I and/or II molecules.

In a further embodiment, immunization results in CD8 and/or CD4 T cell responses.

In a further embodiment, immunization results in the production of cytotoxic T lymphocyte (CTL) responses.

In an embodiment, the DCs activate naïve T cells. Dendritic cells are thought to play at least three distinct roles in priming the immune system to vaccine antigen:

1) MHC class II-restricted presentation of vaccine antigen processed in the exogenous pathway following endocytosis thereof, 2) MHC class I and/or class II-restricted presentation of vaccine antigen following direct transfection of DCs with for example, plasmid DNA encoding the antigen, 3) MHC class-I restricted "cross" presentation of vaccine antigen.

Th1/Th2

In an embodiment, administration of the composition or vaccine of the invention stimulates mediators of humoral and/or cellular immunity.

In an embodiment, administration of the composition or vaccine of the invention results in a cell mediated, Th1-type response.

In another embodiment, administration of the composition or vaccine of the invention results in an antibody mediated, Th2-type response.

In an embodiment, administration of the composition or vaccine of the invention results in the production of Th1-inducing cytokines, such as IL-2, IL-12, IL-15, IL-18 and IFN-γ. These cytokines typically promote cell mediated immunity.

In another embodiment, administration of the composition or vaccine of the invention results in the production of Th2-inducing cytokines, such as IL-4, IL-5 and IL-10. These cytokines typically promote humoral immunity.

In an embodiment, activation of macrophages results in the production of IL-12 and/or IL-18. This in turn may activate IFN-γδ production by NK cells, inducing differentiation to a Th1 mediated immune response which supports cellular mediated immunity and/or production of complement fixing antibodies.

Vaccine

The term "vaccine composition" refers to a composition that can be used to elicit protective immunity in a recipient subject. It should be noted that to be effective, a vaccine of the invention can elicit immunity in a portion of the population, as some individuals may fail to mount a robust or protective immune response, or, in some cases, any immune response to the vaccine. This inability may stem from the individual's genetic background or because of an immunodeficiency condition (either acquired or congenital) or immunosuppression (e.g., treatment with immunosuppressive drugs to prevent organ rejection or suppress an autoimmune condition). Efficacy can be established in animal models.

The vaccine may be "monovalent" (also called univalent) or "multivalent" (also called polyvalent). A monovalent vaccine comprises a single antigen. A multivalent or polyvalent vaccine comprises two or more antigens that may, for example, immunize against two or more strains of the same pathogen, or against two or more pathogens.

The composition or vaccine can be used to immunize, tolerize, treat or protect a subject against, for example, a pathogen or a tumor.

The term "immunize" is used herein to mean generate a protective immune response in a subject, to provide the subject with resistance against a specific pathogen or disease.

The term "tolerize" is used herein to mean induce immunological tolerance in a subject. To tolerize a subject is to induce avoidance or suppression of a specific immune response in the subject. Immunological tolerance can be used to prevent or ameliorate, for example, transplant rejection, autoimmunity, or allergic reaction.

The term "treat" is used herein to mean partial or total destruction of pathogen infected cells or tumor cells within a subject, preferably with minimal destructive effects on non-infected cells. Therapeutic administration of a composition of the invention can treat the recipient subject infected by a pathogen or having cancer. In an alternate embodiment, antigen presenting cells, for example macrophages and DCs, are contacted in vitro or ex vivo with a composition of the invention, and then administered to the subject. As persons skilled in the art are aware, a procedure performed in vitro is performed not in a living organism but in a controlled environment. Such in vitro procedures may be done in or on tissue(s) or cells originating from an organism, and are typically referred to as ex vivo procedures.

The term "protect" is used herein to mean prevent infection by a pathogen or the initiation of tumor growth (i.e., to prevent onset of cancer) or to delay onset of the tumor growth. Prophylactic administration of a composition of the invention can protect the recipient subject from said infection or tumor growth.

Antigens

The present invention provides for use of the mannans in combination with at least one antigen in a vaccine composition. The mannans can be mixed with or conjugated to the at least one antigen to generate a protective immune response following vaccination.

By "at least one antigen" it is meant one or more antigen types or antigenic determinants. Further, it will be appreciated by those skilled in the art, that more than one antigen molecule can be conjugated to the mannan polymer (i.e., the conjugate may comprise more than a single antigen molecule conjugated to the mannan polymer and may comprise one or more antigen types or antigenic determinants).

The vaccine can be administered to a subject that has or is susceptible to, or at risk for a disease. The disease may be associated with a pathogen infection. In this embodiment, vaccine administration may prevent or ameliorate the effects of infection by the pathogen.

As used herein, an "antigen" means a substance that has the ability to induce a specific immune response. The antigen may be a whole organism in any of its life cycle stages, inactivated whole organism, fragments or components isolated from the whole organism, lysate of the organism or tumor lysate, specific antigens genetically or synthetically engineered through methods known in the art. In addition, the selected antigen may be derived from either or both a mature whole organism or sporozoites (oocysts).

The antigen for use in compositions and methods of the present invention can also consist of whole cells or sub-cellular fractions thereof. Such cells or sub-cellular fractions thereof may be derived from, for example, a tumor or infected tissue.

Preferred selected antigens include, for example, antigens from:
- pollens;
- allergens, especially those that induce asthma;
- viruses, such as influenza, feline leukemia virus, feline immunodeficiency virus, HIV-1, HIV-2, rabies, measles, hepatitis B, hoof and mouth disease, papilloma virus, cytomegalovirus, herpes simplex, hepatitis A, hepatitis C, HTLV-1 and HTLV-2;
- bacteria, such as the ethiological agents of anthrax, leprosy, tuberculosis, diphtheria, Lyme disease, syphilis, typhoid fever, and gonorrhea;

protozoans, such as *Babeosis bovis, Plasmodium, Leishmania* spp. *Toxoplasma gondii*, and *Trypanosoma cruzi*;

fungi, such as *Aspergillus* sp., *Candida albicans, Cryptococcus neoformans*, and *Histoplasma capsulatum*;

parasites such as helminths; and tumor antigens, such as mucin-1 (MUC-1), carcinoembryonic antigen, prostate-specific membrane antigen, prostate specific antigen, protein MZ2-E, polymorphic epithelial mucin (PEM), folate-binding-protein LK26, truncated epidermal growth factor receptor (EGRF), Thomsen-Friedenreich (T) antigen, telomerase, survivin, Melan-A/MART-1, WT1, LMP2, human papillomavirus (HPV) E6 E7, human epithelial growth factor receptor (HER-2/neu), Idiotype, melanoma associated antigen 3 (MAGE-3), p53, NY-ESO-1, prostatic acid phosphatase (PAP), cancer testis antigens, 5T4, and GM-2 and GD-2 gangliosides.

The antigen can be a protein, peptide, polysaccharide or oligosaccharide (free or conjugated to a protein carrier), or mixtures thereof. The proteins and peptides may be part of an extract or lysate, purified from a natural source, synthesized by means of solid phase synthesis, or may be obtained by means of recombinant genetics. The polysaccharides and oligosaccharides may be isolated from a natural source, or may be synthesized using enzymatic procedures and/or organic synthesis approaches.

An antigen may form part of a fusion protein in order to facilitate expression and purification on production of the fusion protein in recombinant host cells. The non-antigen portion of the fusion protein would generally represent the N-terminal region of the fusion polypeptide with the carboxy terminal sequences comprising antigen sequences. Fusion proteins may be selected from glutathione-S-transferase, β-galactosidase, or any other protein or part thereof, particularly those which enable affinity purification utilizing the binding or other affinity characteristics of the protein to purify the resultant fusion protein. The protein may also be fused to the C-terminal or N-terminal of the carrier protein. The nature of the fusion protein will depend upon the vector system in which fusion proteins are produced. An example of a bacterial expression vector is pGEX, which on subcloning of a gene of interest into this vector produces a fusion protein consisting of glutathione-S-transferase with the protein of interest. Examples of other vector systems which give rise to fusion proteins with a protein of interest are described in Sambrook et al., 1989, supra.

Alternatively, synthetic peptides or polypeptides, optionally coupled to a protein carrier may be used in the invention. Synthetic peptides or polypeptides may be produced in accordance with standard methods.

Useful peptides or polypeptides may comprise an epitope-bearing portion of a polypeptide known to elicit an antibody and/or an antigen-specific CTL response when the whole polypeptide is administered to an animal. The epitope of this polypeptide portion is an immunogenic or antigenic epitope of the polypeptide.

An "immunogenic epitope" is defined as a part of a protein that elicits an antibody and/or an antigen-specific CTL response when the whole protein is the immunogen. On the other hand, a region of a protein molecule to which an antibody or MHC molecule can bind is defined as an "antigenic epitope". The number of immunogenic epitopes of a protein generally is less than the number of antigenic epitopes.

With regard to the selection of peptides or polypeptides bearing an antigenic epitope, it is well known in that art that relatively short synthetic peptides that mimic part of a protein sequence routinely elicit antiserum that reacts with the partially mimicked protein (see, for example, Sutcliffe et al., 1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention preferably contain a sequence of at least seven, more preferably at least nine and most preferably between about 15 to 30 amino acids contained within the amino acid sequence of a particular polypeptide.

Epitopes recognized by the T-cell receptors on CTLs may be different from those seen by antibodies. Usually, CTLs recognize peptides (derived from proteins enzymatically degraded in the cytosol compartment) which are bound to MHC class I molecules and exposed on the cell surface. These CTL-recognized peptides bind selectively to MHC class I molecules according to MHC allele-specific sequence motifs. These peptides can be identified by expression cloning (see, van der Bruggen, et al., 1991) and predicted using various class I and class II binding peptide algorithms (Pietersz et al., 2006).

Alternatively, CTL-recognized peptides can be identified by induction of cytotoxic T lymphocytes by in vitro or ex vivo stimulation with peptides derived from the protein antigen used for immunization. The particular CTL-recognized epitope-bearing peptides and polypeptides of the invention are preferably sequences of at least six amino acids, and more preferably between about 7 to 20 amino acids.

Epitope-bearing peptides and polypeptides may be produced by any conventional means.

Bacterial Antigens

The antigen can be derived from bacteria, including but not limited to, *Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospira* spp., *Hemophilus ducreyi, Corynebacterium diphtheria, Bordetella pertussis, Bordetella parapertussis, Bordetella bronchiseptica, hemophilus influenza, Escherichia coli, Shigella* spp., *Erlichia* spp., and *Rickettsia* spp.

The bacterial antigen can be native, recombinant or synthetic. Such bacterial antigens include, but are not limited to, selectins or lectins from bacteria that bind to carbohydrate determinants present on cell surfaces, and bacteria receptors for proteins, such as fibronectin, laminin, and collagens.

Viral Antigens

The antigen can be derived from viruses, including but not limited to, Influenza viruses, a Parainfluenza viruses, Mumps virus, Adenoviruses, Respiratory syncytial virus, Epstein-Barr virus, Rhinoviruses, Polioviruses, Coxsackieviruses, Echoviruses, Rubeola virus, Rubella virus, Varicell-zoster virus, Herpes viruses (human and animal), Herpes simplex virus, Parvoviruses (human and animal), Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-1, HTLV-II, FeLV, Bovine LV, FeIV, Canine distemper virus, Canine contagious hepatitis virus, Feline calicivirus, Feline rhinotracheitis virus, TGE virus (swine), and Foot and mouth disease.

Viral antigens can be native, recombinant or synthetic. Such viral antigens include, but are not limited to, viral proteins that are responsible for attachment to cell surface receptors to initiate the infection process, such as (i) envelope glycoproteins of retroviruses (HIV, HTLV, FeLV and others) and herpes viruses, and (ii) the neuramidase of influenza viruses.

Tumor Antigens

In an embodiment of the invention, the subject has cancer or is at increased risk of developing cancer.

By "cancer" it is meant any of various malignant neoplasms, characterized by the proliferation of cells that have the capability to invade surrounding tissue and/or metastasize to new colonisation sites. The cancer may be, for example, breast, gastric, colorectal, pancreatic, bladder or lung cancer. In a preferred embodiment, the cancer is breast cancer.

Many "risk factors" for cancer are well established such as familial history of cancer, personal history of cancer, previous biopsy detection of proliferative disease such as atypical hyperplasia. Particular genetic risk factors are also known, examples for breast cancer include BRCA1, BRCA2, ATM, CHEK-2 and p53 mutations. Lifestyle-related risk factors can also be considered. Lifestyle-related risk factors for breast cancer in women include delayed childbirth until after age 30 and long-term use of hormone replacement therapy. A skilled medical practitioner can evaluate these and other risk factors to determine whether a subject will benefit from prophylactic use of a vaccine composition of the invention.

Cancer vaccines of the invention may comprise one or more tumor associated antigens. Tumor associated antigens can be native, recombinant or synthetic. Such tumor associated antigens include, but are not limited to, MUC-1 and peptide fragments thereof, protein MZ2-E, polymorphic epithelial mucin, folate-binding protein LK26, MAGE-1 or MAGE-3 and peptide fragments thereof, Human chorionic gonadotropin (HCG) and peptide fragments thereof, Carcinoembryonic antigen (CEA) and peptide fragments thereof, Alpha fetoprotein (AFP) and peptide fragments thereof, Pancreatic oncofetal antigen and peptide fragments thereof, CA 125, 15-3, 19-9, 549, 195 and peptide fragments thereof, Prostate-specific antigens (PSA) and peptide fragments thereof, Prostate-specific membrane antigen (PSMA) and peptide fragments thereof, Squamous cell carcinoma antigen (SCCA) and peptide fragments thereof, Ovarian cancer antigen (OCA) and peptide fragments thereof, Pancreas cancer associated antigen (PaA) and peptide fragments thereof, Her1/neu and peptide fragments thereof, gp-100 and peptide fragments thereof, mutant K-ras proteins and peptide fragments thereof, mutant p53 and peptide fragments thereof, nonmutant p53 and peptide fragments thereof, truncated epidermal growth factor receptor (EGFR), chimeric protein p210BCR-ABL, telomerase and peptide fragments thereof, suvivin and peptide fragments thereof, Melan-A/MART-1 protein and peptide fragments thereof, WT1 protein and peptide fragments, LMP2 protein and peptide fragments, HPV E6 E7 protein and peptide fragments, HER-2/neu protein and peptide fragments, Idiotype protein and peptide fragments, NY-ESO-1 protein and peptide fragments, PAP protein and peptide fragments, cancer testis proteins and peptide fragments, and 5T4 protein and peptide fragments. Other exemplary tumor antigens are described in Cheever et al., 2009.

Mucin

In a preferred embodiment, the antigen is a mucin or antigenic fragment or immunogenic mutant/derivative thereof. Many cancers are accompanied by overproduction of human mucin. Mucins are heavily glycosylated proteins (greater than about 100 kDa) which are produced by many epithelial cells and tumours. Mucins found on cancer cells are different in some respects to those on normal epithelial cells, in that some mucins have a deficiency in their carbohydrate coat which leaves the protein core exposed. There are 21 forms of known human mucin designated MUC-1, MUC-2, MUC-3, MUC-4, MUC-5 MUC-6 and MUC-7, etc. MUC-1 is the most ubiquitous. The various mucins all have very similar properties, that is, they are transmembrane glycoproteins, all having a variable number of repeated amino acid sequences, which have a high content of serine, threonine and proline. Overproduction of aberrantly glycosylated mucins (either non-glycosylated or a deficiency in glycosylation) is characteristic of tumours of the breast, ovary, pancreas, colon, lungs, prostate and other tumours of secretory tissue. The cDNA sequences of the respective protein cores of the human mucins MUC-1 to MUC-21 have been cloned and characterized and have been found to contain highly repetitive central portions of varying numbers of repeats of particular amino acid motifs (known as VNTR's). By way of example, MUC-1 consists of unique amino and carboxyl terminal sequences separated by a highly repetitive central portion containing forty to eighty tandemly arranged copies or repeats of a twenty amino acid motif.

In an embodiment, the tumor associated antigen is any one ore more of the human mucins MUC-1 through MUC-21 which, as mentioned above, all comprise highly repetitive central portions of repeated amino acid sequences which are high in serine, threonine and proline. In particular, the vaccines of the invention may comprise a human mucin polypeptide (containing a variable number of repeats associated with normal allelic variation), or may comprise one or more of the repeated sequences of human mucin, preferably two to eighty, more preferably two to twenty and even more preferably two to ten repeated subunits of human mucin. The human mucin and subunits thereof are preferably non-glycosylated or aberrantly glycosylated so as to provoke an immune response to the mucins found on cancer cells which have a deficiency in their carbohydrate coat which leaves the protein core exposed. The use of human mucin MUC-1 is particularly preferred although it is to be clearly understood that the invention extends to the use of any antigen and especially to the use of the human mucins MUC-1 through MUC-21.

The MUC-1 antigen may be as described in, for example, WO 95/108145, U.S. Pat. No. 6,054,438, U.S. Pat. No. 6,222,020, WO 98/50527, WO 01/18035, WO 00/63363, WO 95/03825, WO 00/06723 and WO 04/016643. Use of the MUC-1 T cell epitope-derived peptides or peptide analogues disclosed in WO 2008/011672 is also contemplated.

Mannan-Antigen Conjugates

Delivery of the at least one antigen to, for example, macrophages and DCs can be increased when the at least one antigen is conjugated to the mannans. Although not wishing to be limited by theory, this is most likely because macrophages and DCs have cell surface receptors that recognize carbohydrate moieties (typically from microorganisms) and mediate phagocytosis, as well as pinocytosis, two processes that are involved in antigen presentation. As such, mannan-antigen conjugates of the invention provide an effective mechanism for APC targeting.

In a preferred embodiment, the polysaccharide chains of the mannans are oxidized with, for example, NaIO$_4$ prior to conjugation to the at least one antigen (see schematic of FIG. 4). In an embodiment, the at least one antigen is conjugated to the oxidized mannans in a similar manner to that described in WO 95/18145. Reduced mannans may also be used, and a composition containing this may be prepared by adding sodium borohydride or sodium cyanoborohydride to oxidized mannan-antigen conjugates.

In an alternate embodiment, the polysaccharide chains of the mannans may be first activated with cyanogen bromide and the activated polysaccharide chains then reacted with a diamine, followed by conjugation to the at least one antigen to form conjugates which may optionally then be oxidized.

The mannans and the at least one antigen may be derivatized with bifunctional agents in order to cross-link the mannans and the at least one antigen. Commonly used crosslinking agents include 1,1-bis(diazoacetyl)-2-phenylethane, glutaraldehyde, N-hydroxysuccinimide esters, for example, esters with 4-azidos alicyclic acid, homobifunctional imidoesters including disuccinimidyl esters such as 3,3'-dithiobis(succinimidyl-propionate), and bi functional maleimides such as bis-N-maleimido-1,8-octane. Derivatizing agents such as methyl-3-[(p-azido-phenyl)dithio]propioimidate yield photoactivitable intermediates which are capable of forming cross-links in the presence of light. Oxidized mannans may be reacted with hydrazine derivatives of antigens to give the conjugates. Alternatively, the mannans may be first reacted with reagents such as carbonyl diimidazole, then reacted with antigen, and oxidized to give the conjugates.

The coupling of the at least one antigen to the mannans involves reacting the functional groups on the carbohydrate with functional groups on the antigen. Carbohydrate polymers are replete with hydroxyl groups. These groups may be activated according to standard chemical procedures. For example, hydroxyl groups may be reacted with hydrogen halides, such as hydrogen iodide, hydrogen bromide and hydrogen chloride to give a functionalized halogenated polysaccharide. Hydroxy groups may be activated with phosphorous trihalides, active metals (such as sodium ethoxide, aluminium isopropoxide and potassium tert-butoxide), or esterified (with groups such as tosyl chloride or acetic acid) to form functional groups which can be then be reacted with functional groups on the polypeptide to form one or more bonds.

Nucleic Acid Encoding for Antigen

In an embodiment, the vaccine composition comprises a nucleic acid encoding the antigen. Multiple nucleic acids can be incorporated into the vaccine to produce a polyvalent antigen vaccine. In an embodiment, the vaccine is a DNA vaccine.

At least one nucleic acid can be linked to the mannans, for example, via polycations such as poly-L-lysine, polyethyleneimine, or a PAMAM dendrimer. In an embodiment, the positive charges of oxidized mannan-polycation interact with negatively charged DNA and form a polyplex that can be used for transfection (Tang et al., 2008; Tang et al., 2007; Tang et al., 2009).

DNA vaccination typically involves the direct in vivo introduction of DNA encoding an antigen into, for example, the muscle or skin of the subject for expression of the antigen by the cells of the subject. Once the DNA encoded antigen is processed and presented by the transfected cells, a cellular and/or humoral immune response may be provoked. DNA vaccines are described in U.S. Pat. No. 5,939,400, U.S. Pat. No. 6,110,898, WO 95/20660 and WO 93/19183.

To date, most DNA vaccines in mammalian systems have relied upon viral promoters derived from cytomegalovirus (CMV). These have had good efficiency in both muscle and skin inoculation in a number of mammalian species. A factor known to affect the immune response elicited by DNA immunization is the method of DNA delivery, for example, parenteral routes can yield low rates of gene transfer and produce considerable variability of gene expression. High-velocity inoculation of plasmids, using a gene-gun, enhanced the immune responses of mice, presumably because of a greater efficiency of DNA transfection and more effective antigen presentation by DCs. Vectors containing the nucleic acid-based vaccine of the invention may also be introduced into the desired host by other methods known in the art, for example, transfection, electroporation, microinjection, transduction, cell fusion, DEAE dextran, calcium phosphate precipitation, lipofection (lysosome fusion), or a DNA vector transporter. Mechanisms of administration of DNA vaccines are described in more detailed below.

Other Components

The compositions of the invention may include at least one pharmaceutically acceptable carrier. The term "pharmaceutically acceptable carrier" refers to molecular entities and compositions that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, excipients, solvents, surfactants, suspending agents, buffering agents, lubricating agents, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the invention.

The carrier can be any of those conventionally used and is limited only by chemico-physical considerations, such as solubility and lack of reactivity with the active agent, and by the route of administration. Suitable carriers for this invention include those conventionally used, for example, water, saline, aqueous dextrose, lactose, Ringer's solution, a buffered solution, hyaluronan, glycols, starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like. Liposomes may also be used as carriers.

Compounds which may further enhance the immunogenicity or effectiveness of the compositions of the invention may also be included therein, or be co-administered therewith. For instance, the compositions may comprise one or more oils (for example, Freund's Complete and Incomplete), saponins, modified saponins, liposomes, mineral salts (for example, AlK(SO$_4$)$_2$, AlNa(SO$_4$)$_2$, AlNH$_4$(SO$_4$), silica, alum, Al(OH)$_3$, Ca$_3$(PO$_4$)$_2$, kaolin, and carbon), polynucleotides (for example, poly IC and poly AU acids), and certain natural substances (for example, lipid A, wax D from *Mycobacterium tuberculosis*, as well as substances found in *Corynebacterium parvum*, *Bordetella pertussis*, and members of the genus *Brucella*), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained from natural or recombinant sources according to methods known to those skilled in the art. Other known immunogenic macromolecules include polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenyl-methane-3,3'-dicarboxylic acid and 4-nitro-2-aminobenzoic acid or glycolipids, lipids or carbohydrates.

Administration

The composition or vaccine of the invention can be administered to the subject by an appropriate route, either alone or in combination with another compound.

In an embodiment, the compound is an antigen or nucleic acid encoding therefor. In an embodiment, the mannans and the at least one antigen, or the nucleic acid encoding therefor, are administered sequentially or simultaneously in different compositions. In a preferred embodiment, they are administered in the same composition.

The mannans may be administered in admixture with the at least one antigen or nucleic acid encoding therefor or alternatively, the mannans can be conjugated to the at least one antigen or to the nucleic acid encoding therefor.

A variety of routes of administration are possible including, but not limited to, oral, dietary, topical, parenteral (e.g., intravenous, intra-arterial, intramuscular, intradermal, intravascular or subcutaneous injection), and inhalation (e.g., intrabronchial, intranasal or oral inhalation, intranasal drops) routes of administration.

In one embodiment, the composition or vaccine is administered to a mucosal site. Examples of mucosal sites, include but are not limited to the respiratory tract such as the nasal region (e.g., the nose), the trachea, bronchi and the lungs, the buccal or oral tissues including the oral (e.g., the mouth and gingivae) and oro-pharyngeal cavities, the throat including the tonsils, the conjunctiva of the eyes, the gastrointestinal tract (e.g., oesophagus, stomach, duodenum, small and large intestines, colon and rectum), the reproductive tract/tissues (including but is not limited to the bladder, ureter, urethra and associated tissues, the penis, the vulva/vagina and cervico-vaginal tissues, as well as the uterus and fallopian tubes).

Formulation of the composition or vaccine to be administered will vary according to the route of administration selected (e.g., solution, emulsion, capsule).

The composition or vaccine can be prepared in a physiologically acceptable carrier. For solutions or emulsions, suitable carriers include aqueous or alcoholic/aqueous solutions, emulsions or suspensions, including saline and buffered media. Parenteral carriers include sodium chloride solution, Ringer's dextrose, dextrose and sodium chloride, lactated Ringer's or fixed oils. Intravenous carriers include various additives, preservatives, or fluid, nutrient or electrolyte replenishers and the like (See, generally, Remington's Pharmaceutical Sciences, 1985). For inhalation, a soluble composition or vaccine can be loaded into a suitable dispenser for administration (e.g., an atomizer, nebulizer or pressurized aerosol dispenser).

A nucleic acid encoding the antigen can be directly delivered to cells by incorporation into a retroviral, adenoviral or other suitable vector, or various other protein-based or lipid-based gene delivery complexes, as well as through use of techniques facilitating the delivery of "naked" polynucleotides (such as electroporation or "gene gun" delivery). Alternatively, the nucleic acid can be introduced into a host cell capable of expressing the protein for delivery. These transfected or transformed cells can then be implanted (alone or in a barrier device), injected or otherwise introduced in an amount effective to express the antigen in a therapeutically effective amount.

In an alternate embodiment, antigen presenting cells, for example macrophages and/or DCs can be contacted in vitro or ex vivo with a composition to effect loading with antigen and then be administered to the subject. In one embodiment, the antigen presenting cells are derived from the subject or an autologous donor and loaded with antigen ex vivo. For example, blood may be taken from the subject or autologous donor and enriched for peripheral blood mononuclear cells (PBMCs) by density gradient centrifugation, followed by adherence to a plastic surface to enrich monocytes. Adherent cells can then be cultured with a cytokine mix to induce differentiation to for example, immature DCs, and the resulting immature DCs can be contacted with the vaccine antigen and mannans or alternatively, transfected with nucleic acid encoding said antigen. Aliquots (for example, cryopreserved aliquots) of the resultant mature/activated dendritic cell preparations (i.e., having upregulated costimulatory molecules CD40, CD80 and CD86) can then be administered to the subject by, for example, intradermal injection(s) on a protocol defined schedule.

Administration of the composition or vaccine may be a single or multiple event, or may be part of a prime-boost protocol, a combination of these, or each of these with other, conventional methods of administration/vaccination. The prime-boost protocol may, for example, comprise priming by, for example, intramuscular, intradermal, intravascular subcutaneous, or intravenous administration, and boosting by for example, intranasal, intramuscular, intradermal, intravascular subcutaneous, or intravenous administration. One or both of the priming and boosting composition may include the antigen or nucleic acid encoding therefor and mannans. One of the priming and boosting compositions may omit the mannans.

The amount and frequency of administration of the composition or vaccine of the invention effective for a particular application will vary according to factors known in the art including but not limited to, the physical and chemical nature of the mannans and/or the at least one antigen or nucleic acid encoding therefor, the nature of the carrier, the intended dosing regimen, the state of the subject's immune system (e.g., suppressed, compromised, stimulated), the method of administering the composition or vaccine, and the species to which the composition or vaccine is being administered. Accordingly, it is not practical to set forth generally the amount of mannans and/or the at least one antigen or nucleic acid encoding therefor effective for all possible applications. The amount and frequency may be determined by an attending physician or veterinarian.

An effective amount of the composition is administered. An "effective amount" is an amount sufficient to achieve the desired immunostimulatory effect, under the conditions of administration.

By way of example, from about 100 ng/kg to about 50 mg/kg mannans may be administered to the subject, preferably from about 10 µg/kg to about 10 mg/kg. Even more preferably, a dose of from about 1 mg/kg to about 10 mk/kg mannans is contemplated, particularly for humans.

By way of example, from about 1 µg/kg to about 10,000 µg/kg antigen may be administered to a subject, preferably from about 5 µg/kg to about 5000 µg/kg, more preferably from about 8 µg/kg to about 1000 µg/kg and most preferably, from about 400 µg/kg to about 600 µg/kg. Even more preferably, a dose of from about 100 µg/kg to about 200 µg/kg antigen is contemplated, particularly for humans.

The composition and vaccine of the invention may also be administered to subjects in conjunction with other immune response modifiers, for example cytokines, HLA class II protein-binding helper molecules, CD40 agonists, antagonists of checkpoint receptors (for example, CTLA-4, PD-1, Stat3), B7 costimulatory molecules, FLt3 agonists, and CD40L agonists.

The presence of a HLA class II protein-binding helper molecule is effective in stimulating helper (CD4$^+$) T cells. The HLA class II protein-binding helper molecule may be any of those well known to persons skilled in the art including, for example, keyhole limpet haemocyanin (KLH), tetanus toxoid (TT), diphtheria toxoid, or smaller T cell helper epitopes, such as PADRE peptides, and combinations thereof.

Compounds which may further enhance the immunogenicity or effectiveness of the compositions of the invention and/or pharmaceutically acceptable carriers may also be included therein, or be co-administered therewith.

The compositions of the invention can also be used in combination with other immunotherapy strategies, for example, chemotherapy where the subject has cancer and the vaccine is a cancer vaccine.

Delivery of a Nucleic Acid to a Cell

In an embodiment, the invention relates to a composition for delivering a nucleic acid to a cell, the composition comprising at least one nucleic acid and mannans, wherein at least 75% of the mannans are greater than about 1000 kDa. The at least one nucleic acid may be conjugated to the mannans via polycations.

In an embodiment, the nucleic acid encodes an antigen.

In another embodiment the nucleic acid encodes a gene.

The phrase "introducing a nucleic acid to a cell" refers to introducing nucleic acid sequences by recombinant means.

The term "nucleic acid" is synonymous with DNA, RNA and polynucleotides in all their forms, i.e., single and double-stranded DNA, cDNA, mRNA, siRNA and the like.

Means of delivery of nucleic acids to a subject include direct delivery of the nucleic acid and delivery of cells transfected or transformed with the nucleic acid. Cells or nucleic acids can be delivered directly to the desired organ or tumor, for example by injection, catheterization, or endoscopy. They can also be delivered intravenously, intrabronchially, intra-tumorally, intrathecally, intramuscularly, intraocularly, topically, subcutaneously, transdermally or per os.

Examples of nucleic acid delivery vehicles are liposomes, biocompatible polymers, including natural polymers and synthetic polymers, lipoproteins, polypeptides, polysaccharides, lipopolysaccharides, artificial viral envelopes, metal particles, and bacteria, viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy, genetic vaccination (for example, DNA vaccination), as well as for simple protein expression.

As used herein, "vector" refers to discrete elements that are used to introduce heterologous nucleic acid into cells for either expression or replication thereof. For example, a vector may be an artificial chromosome, plasmid, cosmid, bacteriophage or virus, and may be capable of stable integration into a host cell genome, or it may exist as an independent genetic element (e.g., episome, plasmid). A vector may exist as a single polynucleotide or as two or more separate polynucleotides. Vectors may be single copy vectors or multicopy vectors when present in a host cell. Preferred vectors for use in the present invention are expression vectors in which one or more functional genes can be inserted into the vector, in proper orientation and proximity to expression control elements so as to direct expression of one or more proteins in the host cell.

The term "control elements" refers to nucleic acid sequences necessary for the expression of an operably linked nucleotide coding sequence in a particular host cell. The control sequences suitable for expression in prokaryotes, for example, include origins of replication, promoters, ribosome binding sites, and transcription termination sites. The control sequences that are suitable for expression in eukaryotes, for example, include origins of replication, promoters, ribosome-binding sites, polyadenylation signals, and enhancers.

A "promoter" directs transcription of a nucleic acid. As used herein, a "promoter" includes necessary nucleic acid sequences near the start site of transcription, such as, in the case of a polymerase II type promoter, a TATA element.

A promoter also optionally includes distal "enhancer or repressor elements", which can be located as much as several thousand base pairs from the start site of transcription. The promoter can either be homologous or heterologous. A "constitutive" promoter is a promoter that is active in a selected organism under most environmental and developmental conditions. An "inducible" promoter is a promoter that is under environmental or developmental regulation in a selected organism.

The vector may be a viral or non-viral vector, including adenovirus vectors, adeno-associated virus vectors, retrovirus vectors, lentivirus vectors, and plasmid vectors. Exemplary types of viruses include HSV (herpes simplex virus), adenovirus, AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers. Gene delivery, gene transfer, and the like, as used herein, are terms referring to the introduction of a nucleic acid (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of nucleic acids). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

EXAMPLES

Example 1

Materials and Methods

Media & Chemicals

Complete RPMI-1640 media was prepared by supplementing with 2% HEPES, 0.1 mM 2-mercaptoethanol, 100 U/ml penicillin, 100 µg/ml streptomycin, 2 mM glutamine and 10% (v/v) fetal calf serum. Recombinant GM-CSF used to culture DCs was purchased from BD-Pharmingen (San Diego, USA) and was reconstituted in PBS. Lipopolysaccharide (LPS) (L3137, Sigma, Castle Hill Australia) was reconstituted in sterile distilled water. Anti-CD11c-APC was purchased from BD Pharmingen (San Diego, Calif.). Anti-CD40, CD80 and CD86 antibodies were prepared in-house. Mannan, NaIO$_4$, ANTS, ethane-1,2-diol were purchased from Sigma.

The mannan used in these studies is from Bakers yeast (*Saccharomyces cerevisae*). Mannan is very heterogeneous incorporating mannose rich polysaccharides with various molecular weights ranging from 50 to >1,000 kDa.

Fractionation Method

Mannan (Sigma) at 20 mg/ml in double distilled water (DDW) was added to 20 ml 300 kDa MWCO Vivaspin concentrators (Sartorius), centrifuged at 2500 rpm for 15-20 minutes and concentrated down to 1-2 ml (FIG. 1). The concentrator was refilled until the entire sample was added. Several spins were needed. The filtrate was collected and 2×DDW washes were done but discarded. The concentrated fraction (retentate) is the >300 kDa fraction. The filtrate was then applied to 15 ml 100 kDa MWCO Amicon spin concentrator (Millipore) and carried out as detailed previously. The mannan was then sequentially fractionated using 2×15 ml 50 kDa MWCO Amicon spin concentrators (Millipore) followed by 2×15 ml 30 kDa MWCO Amicon spin concentrators (Millipore). This resulted in fractions of >300, 100-300, 50-100, 30-50 and <30 kDa. The retentate fractions and the final filtrate were freeze dried to a white fluffy powder, except with the <30 kDa fraction which was gummy and so not used. The samples were weighed out and recoveries recorded.

In later fractionation runs, 2×20 ml 1000 kDa MWCO Vivaspin concentrators from Sartorius were used as the first fractionation step, followed by the sequence of the other concentrators as mentioned above. This results in fractions of >1000, 300-1000, 100-300, 50-100, 30-50 and <30 kDa.

As before the retentate fractions and the final filtrate were freeze dried to a white fluffy powder, and the <30 kDa fraction was not used. The samples were weighed out and recoveries recorded. In some runs, there was no powder in the 300-1000 kDa fraction and so in those runs that particular fraction was not used for analysis.

Quantitation of Aldehyde Residues in Mannans Using the PDPH Quantitation Method

A method for the quantification of the number of aldehyde groups in oxidized mannan is schematically shown in FIG. 2. The same molar concentration of NaIO$_4$ is used such that the extent of oxidation will depend on the molecular weight of mannan. Mannan and mannan fractions 1.4 mg/0.1 ml in 0.1 M phosphate pH 6.0 buffer were oxidized with 0.01 M NaIO$_4$ and allowed to react for 1 hour on ice in the dark. The reaction was quenched with 10 µl ethane-1,2-diol and allowed to react for a further ½ hour, before passing through a PD10 column with 0.1 M acetate buffer pH 4.8.

One ml of the 2 ml of oxidized mannan at 0.7 mg/ml was reacted with 0.1 mg PDPH rotating overnight at room temperature, before passing through a PD10 with DDW. The number of aldehyde groups can be determined by reacting with 0.01 M DTT for 15 minutes and reading Absorbance at OD343 nm. This releases the 2-pyridine which indicates aldehyde groups (FIG. 2).

$$\text{Number of aldehyde residues} = \frac{\text{concentration of 2-pyridinethione}(M)}{\text{concentration of mannan}(M)}$$

$$= \frac{[OD_{343}/8080]}{\left[\frac{\text{concentration of mannan (mg/ml)}}{\text{Molecular weight of mannan}}\right]}.$$

The average molecular weight used for the various fractions are; whole mannan=500 kDa, >1,000=1000 kDa, >300=650 kDa, 100-300=200 kDa, 50-100=75 kDa, 30-50=40 kDa.

Chemical Modification of Mannans with ANTS and Quantitation

Chemical modification of oxidized mannan with ANTS is schematically shown in FIG. 3. Mannan and mannan fractions 1.4 mg/0.1 ml in 0.1 M phosphate pH 6.0 buffer were oxidized with 0.01 M NaIO$_4$ and allowed to react for 1 hour on ice in the dark. The reaction was quenched with ethane-1,2-diol and allowed to react for a further ½ hour, before passing through a PD10 column with 0.1 M acetate buffer pH 4.8.

One ml of the 0.7 mg/ml of oxidized mannan, >300 kDa, 100-300 kDa, 50-100 kDa and 30-50 kDa fractions were reacted with 0.288, 0.184, 0.598, 1.59 and 2.99 mg ANTS (×400 excess) in 3/17 acetic acid/DDW respectively. Sodium cyanoborohydride (50 µl, 1 M; Sigma) was added and the reaction left rotating overnight at room temperature, before passing through a PD10 with DDW. The fluorescence of the ANTS conjugates were read against an ANTS standard at excitation 405 nm emission 520 nm.

Resorcinol Assay for Quantitation of Mannose Residues

Mannan and mannan fractions were quantitated using the resorcinol assay (Monsigny et al., 1988). Mannose was used as a standard. The plate was read at Absorbance at OD 450 nm (since there is no 430 or 480 nm).

Conjugation of Antigens to Mannan

Conjugation of proteins to oxidized mannan is schematically shown in FIG. 4. Mannan and fractions >1000 kDa, 300-1000 kDa (or >300 in earlier runs), 100-300 kDa, 50-100 kDa, 30-50 kDa at 14 mg/ml in 0.1 M phosphate pH 6.0, (except 30-50 fraction which was at 14 mg/0.5 ml) was oxidized with the addition of 0.1 M NaIO$_4$ 100, 77, 250, 600 µl and 1.25 ml respectively and made up to a final volume of 1.6 ml. The mixture was placed for 1 hour on ice in the dark, quenched with ethane-1,2-diol and further reacted for ½ hour as before. The conjugates were separated on a PD10 column (GE Biosciences) pre-equilibrated with 0.05 M bicarbonate pH 9.0 to remove unreacted material and byproducts. This involved passing the 1.6 ml sample, followed by 0.9 ml buffer through the column and discarded. The next 2 ml was collected and 1 ml of oxidized mannan or fraction was reacted with a calculated amount of 0.35, 0.3, 0.495, 0.735 and 0.59 mg of FP and OVA respectively. The conjugates incubated overnight at room temperature and separated on a 4-12 or 4-20% SDS-PAGE gel to verify successful conjugation. Good conjugation is indicated by a smear and lack of a distinct protein band.

For the final >1000 MFP conjugate used in the in vivo studies 0.7 mg FP (5.45 mg/ml, 128 µl) was reacted with 2 ml oxidized mannan. Similarly, for >1000ManRSVg conjugate 0.25 mg RSVg (0.37 mg/ml, 367 µl) was reacted with 2 ml oxidized mannan.

The molar concentration of mannan in the >1000 MFP is one half of that in MFP, therefore 10 µg FP was used in the in vivo immunogenicity studies.

Native and Denaturing Gel Electrophoresis

Mannan and fractions were visualized on SDS-PAGE or native gels. Precast (PAGE gel) SDS 4-12% or 4-20% gradient gels (PAGE gel) were run in 1×MOPS SDS running buffer. Alternatively, 12% native gels (basic conditions) were used consisting of a 5% stacking gel made in 0.063 M Tris-HCl pH 6.8 and a resolving gel made in TBE. Electrophoresis was performed in TBE plus 0.19 M glycine (Sharma et al., 2003).

Coomassie stain and PAS stain was used to stain gels for protein and sugars respectively.

Molecular Weight Determination of Mannan Fractions by Densitometry

Mannan fractions were oxidized with NaIO$_4$ and labelled with ANTS as above. Samples of ANTS-labelled mannan were analysed by SDS-PAGE after PAS staining. Dried gels were scanned and analysed by densitometry using Quantity One (Bio-Rad) software.

Generation of Bone-Marrow Derived Dendritic Cells

Murine DCs were generated as described previously (Apostolopoulos et al., 2006). Briefly, bone marrow cells were extracted from the lumen of femurs and tibias. Bone marrow cells were then treated with sterile 0.73% (w/v) NH$_4$Cl for 10 minutes at 37° C. to lyze erythrocytes. Cells were washed and resuspended in complete media (2×10$^6$ cells/3 ml) supplemented with 10 ng/ml of GM-CSF. These cells were cultured for 4 days in a 24 well plate (1 ml/well). Cells were harvested by gentle pipetting of the culture media. GM-CSF cultured bone marrow cells yields large numbers of MHC class II expressing DCs that are potent mixed lymphocyte reaction (MLR) stimulator cells.

In Vitro Dendritic Cell Maturation Studies

C57BL/6 mice derived DCs were used in maturation studies. Dendritic cells were removed from culture plates and 1×10$^5$ DCs were resuspended in 150 µl of complete RPMI supplemented with 10 ng/ml GM-CSF and seeded into 48 well plates. Mannan and various mannan fractions were added such that final concentrations of 800, 400, and 200 µg/ml were added to wells. LPS (1 µg/ml) was used as a positive control and was also added into respective wells and incubated at 37° C. for 18 hours. Cells were harvested and stained with anti-CD11c-APC together with anti-CD86, anti-CD40 or anti-CD80 that was conjugated with fluorescein isothiocyanate (FITC). CD11c$^{high}$ cells were gated and intensity of FITC was determined by histogram analysis to determine DC maturation states.

In Vivo Mouse Immunogenicity Studies

Mice and Immunizations

HLA-A2/K$^b$ mice were purchased from the Animal Resources Centre, Perth, Australia. To determine effector immune responses induced by the MFP, >1000 MFP and unconjugated FP, HLA-A2/K$^b$ mice were immunized intradermally in the base of tail with a volume of 100 µl on days 0, 10 and 17 and immune responses assessed 10-14 days later using ELISpot assay. Mice were bled after 2$^{nd}$ and 3$^{rd}$ injection and MUC1-specific total Ig, IgG2a and IgG1 detected by ELISA assay.

Antigen-Specific T Cell Responses In Vivo

Spleen cells from immunized HLA-A2/K$^b$ mice were isolated and assessed by ELISpot for antigen-specific IFN-γ secretion. Mixed acetate plates (MAIP Millipore) were coated overnight with anti-mouse IFN-γ (AN18, 5 µg/ml, Mabtech, Germany). 5×10$^5$ spleen cells/well were added and incubated in 10% FCS RPMI 1640 media in the presence of MUC-FP (20 µg/ml) for 18 hour. ConA (1 µg/ml) or cells alone were used as positive and negative controls, respectively. Cells were discarded and after washing (0.05% Tween 20/PBS), anti-mouse IFN-γ antibody-biotin (R4-6A2, Mabtech, Calif., USA) was added for 2 hours followed by extravidin-alkaline phosphatase (AP) at 0.1 µg/ml (Sigma, UK) for 2 hours at room temperature. Spots of activity were detected using a colorimetric AP kit (Biorad, Hercules, Calif., USA). Cytokine spots were counted with an AID ELISpot Reader system (Autoimmun Diagnostika GmbH, Germany). Data is presented as mean spot forming units (SFU) per 0.5×10$^6$ cells +/− standard deviation of the mean (SD).

Human In Vitro Immunogenicity Studies of Protein Antigens Linked to >1000 kDa Oxidized Mannan Protein/Peptide Antigens MART-1 protein was purchased from Biovision, USA. GST-MUC1-VNTR (FP) was prepared as described in Apostolopoulos et al., 1993. His tagged MUC1-VNTR (pTrc) was prepared in house in the pTrcB vector (Invitrogen) (Loveland et al., 2006). The HLA-A2 epitope peptides specific for Melan-A/MART-1 [EAAGIGILTV (native) (SEQ ID NO:1), ELAGIGILTV (analog) (SEQ ID NO:2)] were synthesized by Genscript, USA.

Conjugation of GST-MUC1-VNTR (FP), MUC1-VNTR (pTrc) and MART-1 to >1000 kDa Oxidized Mannan.

The conjugation of antigens to periodate >1000 kDa oxidized mannan was carried out as described earlier. The ratio of >1000 kDa mannan to antigen was 40:1.

Generation of Peptide-Specific CD8 T Cells.

PBMCs were separated from buffy coats via density gradient centrifugation using Ficoll-Paque PLUS (GE Healthcare). HLA-A2 status was assessed by flow cytometry. PBMC were resuspended at 5×10$^6$/ml in complete AB medium (RPMI1640, 10% AB serum, Pen/Strep, HEPES, L-GLUT, NEAA, Sodium Pyruvate (Invitrogen), 2-mercaptoethanol) and stimulated with 10 ng/ml of MART-1 analog peptide (ELAGIGILTV) (SEQ ID NO:2) and 3 ng/ml R848 (InvivoGen) in a 24 well plate. Three days later, another 1 ml complete AB medium supplemented with 50 U/ml IL-2 (R & D Systems), 20 ng/ml IL-15 and 20 ng/ml IL-7 (Peprotech) was added. Seven-ten days after initial priming, cells were re-stimulated with irradiated autologous PBMCs (1:100) pulsed with 2 ng/ml FMP or 10 µg/ml MART1 analog peptide (ELA). On the following day, 1 ml supernatant was exchanged for fresh complete AB medium containing 25 U/ml IL-2. This was repeated every 3-4 days.

MART-1-specific T cells clones were generated by FACS sorting. IFN' secreting cells specific for ELAGIGILTV peptide (SEQ ID NO:2) were sorted using the FACS Aria following a 4 hour incubation with irradiated (6000 cGy) T2 cells pulsed with peptide. IFNγ secreting cells were identified using the IFNγ secretion and detection assay (Miltenyi Biotech) performed according to manufacturer's protocol.

Priming Protein Antigen-Specific T Cell Responses.

Monocytes were purified from PBMC by AutoMACS separation using CD14 microbeads (Miltenyi Biotech). Monocyte-derived dendritic cells (MoDC) were generated by culturing monocytes (5×10$^5$/ml) in complete FCS medium (RPMI1640+10% FCS+L-GLUT, Pen/Strep, HEPES, non-essential amino acids, sodium pyruvate, 2-mercaptoethanol) containing 50 ng/ml GM-CSF and 20 ng/ml IL-4 (R & D Systems) for 5-6 days in a T75 flask.

MoDC at 2×10$^5$/ml (for 1:20 MoDC:T cell) in complete AB medium were added to a 24 well plate (1 ml per test condition) followed by protein or >1000 kDa oxidized mannan conjugate (10-20 µg/ml). Four hours later, 4×10$^6$ CD14 depleted PBMC were added to the wells in 1 ml complete AB medium. After 3 days, 25 U/ml IL-2, 10 ng/ml IL-7 and 10 ng/ml IL-15 was added. The T cells were re-stimulated 7-10 days later with 1×10$^5$ MoDC loaded with antigen. Twenty four hours following re-stimulation, cultures were supplemented with 25 U/ml IL-2 and again 3-4 days after. T cell cultures were typically analysed after 1 or 2 re-stimulations.

The flow through and washings from each were passed through the next membrane. All separations were done in water and at the end, all samples were lyophilized and weights of the white powders recorded (Table 1).

TABLE 1

A representative sample of fractionation runs showing recovery various fractions and aldehyde residues on oxidized mannan

|  |  | mannan | >300 | 100-300 | 50-100 | 30-50 | <30 |  |
|---|---|---|---|---|---|---|---|---|
| Run 5 | 240 mg |  |  |  |  |  |  |  |
|  | % recovery |  | 11.2 | 7.2 | 17.2 | 16.08 | 7.2 | 58.88 |
|  | Aldehyde residues | 113 | 135 | 113 | 30.7 | 15.9 |  |  |
|  |  | 112 | 135 | 63 | 31 | 16 |  |  |
| Run 6 | 480 mg |  |  |  |  |  |  |  |
|  | % recovery |  | 8.75 | 8.89 | 5.3 | 7.8 | ND | 30.74 |
|  | Aldehyde residues | 74 | 84 | 38 | 21 | 11 |  |  |
| Run 7 | 960 mg |  |  |  |  |  |  |  |
|  | % recovery |  | 6 | 8.5 | 10.3 | 7.2 | ND | 32 |
|  | Aldehyde residues | 73 | 82 | 35 | 19 | 9 |  |  |

Analysis of Antigen-Specific T Cell Responses

For T cell epitope peptides—Peptide loaded T2 cells ($2 \times 10^5$/well) were prepared by pulsing with an irrelevant peptide (e.g., CAP-1 10 μg/ml or no peptide) and one with the peptide of interest (5 μg/ml) for 1 hour in serum free medium with 1.25 μg/ml β2-microglobulin. T2 cells were added at about a 1:5 ratio ($4 \times 10^4$/well) in 100 μl to the duplicate T cell wells and incubate for 1 hour at 37° C. 5% $CO_2$. 50 μl media containing Golgi-Stop (0.1 μl per 200 μl T cell/MoDC co-culture) was added and cells incubated for a further 3-4 hours at 37° C. 5% $CO_2$.

For protein antigen and conjugates—Antigen or >1000 kDa mannan conjugates (20 μg/ml) were added to v-bottom 96 well cluster plate containing $2 \times 10^4$ MoDC/well (autologous or A2 matched) in 75-100 μl complete medium and incubated for 2 hours. $2 \times 10^5$ stimulated T cells in 75-100 μl complete medium were added to each well and cells incubated for 15-16 hours at 37° C. 5% $CO_2$. 50 μl media containing Golgi-Stop (0.1 μl per 200 μl T cell/MoDC co-culture) was added and cells incubated for a further 4-5 hours at 37° C. 5% $CO_2$.

Analysis of Intracellular Interferon-Gamma (IFNγ) Responses

Cells were stained for surface markers CD8 and CD4, fixed and permeabilised, then stained for accumulation of intracellular IFNγ using CD4 APC-Cy7, CD8 FITC and IFNγ PE-Cy7 (BD) with the Cytofix/CytoPerm Kit (BD). Antigen-specific T cells were identified by flow cytometry comparing IFNγ+CD4 and CD8 T cells in the presence of the peptide/protein of interest with the irrelevant peptide/protein controls.

Example 2

Fractionation of Mannan

Initially, mannan was sequentially passed through membranes as described in the Materials and Methods to isolate >300 kDa, 100-300 kDa, 50-100 kDa, 30-50 kDa, 4-30 kDa mannan fractions. Subsequently, mannan fractions >1,000 kDa, 100-300 kDa, 50-100 kDa and 30-50 kDa were isolated. The 4-30 kDa fraction was like a gum like residue so not included in the subsequent studies.

Separation was done by sequentially fractionating a known volume of mannan at a known concentration through 300 kDa, 100 kDa, 50 kDa, 30 kDa membranes (FIG. 1).

The various fractions were analysed for aldehyde residues generated after reaction with 0.01 M $NaIO_4$ as described in the methods. As shown in Table 1, the whole mannan, >300 kDa, 100-300 kDa, 50-100 kDa and 30-50 kDa fractions yield 73, 82, 35, 19 and 9 aldehyde residues respectively (e.g., run 7).

Example 3

Binding of Various Mannan Fractions to Mannose Receptor

Huh-7 cells are human hepatocellular carcinoma cells that express mannose receptors. Mannose-BSA is known to bind the mannose receptor and was included as a positive control in these studies. Whole mannan and the various fractions were labelled with FITC and the binding to huh-7 cells observed by flow cytometry (FIG. 5).

Whole mannan and all fractions bound huh-7 cells in a dose dependent manner. Therefore, regardless of the size all mannan fractions bind the mannose receptor or other mannose binding lectins.

Example 4

Activation of BMDC by Mannan and Various Fractions of Mannan

To ascertain if the various fractions of mannan activate BMDC and if any fraction is superior to whole mannan, fractions were incubated with DCs at different doses and for different times, and maturation markers CD40, CD80 and CD86 was monitored by flow cytometry (FIG. 6). As shown in FIG. 6 all fractions activated DCs in a dose and time dependent manner. The >300 kDa fraction was superior to whole mannan.

Example 5

Isolation of >1000 kDa Mannan Fraction

Since the >300 kDa fraction of mannan activated BMDCs more effectively than whole mannan, a higher molecular weight fraction was isolated for analysis. In order to isolate an even higher molecular weight fraction, the whole mannan was passed through a Centriprep concentrator with 1,000 kDa cut-off membrane. The yield of the various fractions are shown in Table 2. Interestingly, the 300-1,000 kDa fraction was vastly reduced indicating that >1,000 kDa mannans dominate the previously isolated >300 kDa mannan fraction.

Example 6

Comparison of the Activity of the >1000 kDa Mannan Fraction with Whole Mannan and the >300 kDa Mannan Fraction The ability of the various doses of the >1000 kDa fraction to stimulate BMDC was measured by observing the upregulation of CD40 and CD86 after a 48 hour period by flow cytometry (FIGS. 7A and 7B, respectively). The >1000 kDa fraction was compared to the >300 kDa fraction and whole mannan and it was apparent that the >1000 kDa fraction was superior to whole mannan and similar to the >300 kDa fraction.

the fractionated molecular weight (membrane cut-off) (FIG. 10). The SDS-PAGE gels were scanned and used for densitometric analysis (FIG. 11). Regular protein standards were also used. This enables molecular weight ranges to be assigned to bands which unlike defined proteins are spread (broad bands). Mannans from several fractionation runs were analyzed to validate the analysis. Standard curves were generated from known molecular weight (protein or mannan fractions) and the relative front (Rf). The Rf is defined as the total distance migrated divided by the distance migrated by the specific band (FIG. 12). Based on the standard curves, the relative molecular weights of the various mannan fractions were calculated (FIGS. 13 and 14).

Example 8

Conjugation of MUC1-FP to Mannan

The various fractions of mannan were conjugated to MUC1-FP as described in the methods. Since the molecular

TABLE 2

Representative example of a fractionation run isolating a >1000 kDa mannan fraction

| Fractionation | Bottle/Batch | | | mannan | >1000 | 300-1000 | 100-300 | 50-100 | 30-50 | <30 | Recovery |
|---|---|---|---|---|---|---|---|---|---|---|---|
| 8 | Batch 2 | 985.5 mg | | | | | | | | | |
| | 102K37781 | % recovery | | | | 3.6 | 0 | 4.9 | 10.4 | 7.3 | 26.1 |
| | | Aldehyde residues | | 106 | 205 | | 44 | 16 | 8.8 | | |
| 9 | Batch 2 | 1019 mg | | | | | | | | | |
| | 102K37781 | % recovery | | | | 6.7 | 0 | 20 | 14.7 | 7.5 | 48.9 |
| | | Aldehyde residues | | 108 | 228.9 | N/A | 42 | 19.7 | 10.6 | | |
| 10 | Batch 7 | 1007 mg | | | | | | | | | |
| | 048K3810 | % recovery | | | | 31 | 0.26 | 20 | 0.49 | 2.3 | 53.7 |
| | | Aldehyde residues | | 115 | 219 | 111 | 39.8 | 21 | 8.1 | | |
| 11 | Batch 7 | 1063 mg | (end-) | | | | | | | | |
| | 048K3810 | % recovery | | | | 37 | 0 | 12 | 0.87 | 0.36 | 53 |
| | | Aldehyde residues | | 95 | 218 | N/A | 39.8 | 15 | 7.2 | | |

Example 7

Analysis of Molecular Weight of Mannan Fractions

As seen above, the various fractions of mannan can activate BMDC, bind to the mannose receptor and the >1000 kDa mannan fraction is the most biologically active fraction. However, it is important to be able to analyze the biochemical properties of the fractions, as well as obtain relative molecular weights of the fractions so that a set of specifications can be set. The present inventors have already shown that the various mannans generate different numbers of aldehyde groups when oxidized with NaIO$_4$ (Tables 1 and 2).

The resorcinol assay that measures the mannose content of mannan can also be used as a means of identification of the different fractions of mannan (FIG. 8).

Mannans are carbohydrates without charges and highly hydrophilic and as a result do not migrate on SDS-PAGE gels used for protein analysis. Frequently, carbohydrates are chemically modified to incorporate charges and hydrophobic properties for analysis. To incorporate these properties, the oxidized mannans were reacted with ANTS. Analysis of the mannan fractions labelled with ANTS on native PAGE gel (FIG. 9) did not resolve the mannans based on their relative molecular weights.

However, when the ANTS labelled fractions were analysed by SDS-PAGE, they migrated in a pattern similar to weights and the number of aldehyde groups generated are different in the whole mannan compared with the fractions, the amount of FP used was standardized as the molar ratio of MUC1-FP to the aldehydes. In addition, a range of amounts of MUC1-FP was conjugated and analysed by SDS-PAGE (FIG. 15).

Example 9

In Vivo Activity of >1000 MFP and MFP in Mice

Whole mannan and >1000 kDa mannan were prepared as described above and used for in vivo immunogenicity studies.

To ascertain the immunogenicity of MUC1 linked to whole mannan, >1000 kDa mannan, conjugates or MUC1-FP were injected intradermally into mice at a dose of 10 μg on day 0, 10, 17 and 14 days. Mice were euthanized to analyze cellular responses by ELISpot analysis (FIG. 16). Antigen specific IFN-γ responses to various doses of MUC1-FP were measured in splenocyte cultures from immunized mice. As shown in FIG. 16, the cellular responses were not significantly different between the MUC1-FP, MFP and >1000 MFP immunized mice. The serum from immunized mice was tested for anti-MUC1-specific total IgG, IgG1 and IgG2a antibodies (FIG. 17). Interestingly, the mice immunized with the >1000 MFP had a ~10 fold higher titre of anti-MUC1-specific IgG2a in comparison to the other groups. A similar IgG2a bias was demonstrated in serum from mice after 2 immunizations (data not shown).

Example 10

Characterisation of Mannan and Possible Quality Control Assays

Mannan is currently sourced from Sigma. It is not of good manufacturing practice (GMP) standard and the only information given is shown in FIG. 18. It will be important to the yeast mannan if it is bought from a manufacturer to ensure it meets a particular standard. The PDPH assay could be used to measure aldehydes, the resorcinol assay to measure mannose content and ANTS assay to characterize the various batches of mannan.

Five batches of mannan from Sigma were analyzed using the resorcinol assay. As showed in FIG. 19A, all batches displayed the same absorbance versus concentration curve, indicating the same mannose content in mannans. FIG. 19B shows the standard curve using mannose in the resorcinol assay. Similarly all 5 batches were analyzed for aldehyde residues after oxidation with NaIO$_4$ (FIG. 20).

From three independent measurements, it can be seen that the number of aldehyde residues vary between 90-155 residues. Therefore, the specification for mannan could be set as pass, if the aldehyde residues generated is 125±20%. In a similar manner, the oxidized mannan can be reacted with ANTS instead of PDPH for measurement of fluorescence (FIG. 21). Interestingly, the variation in all the batches in this assay is also ~±20%.

Example 11

GST-MUC1-VNTR (FP)

Conjugation

FP was conjugated to >1000 kDa oxidized mannan (>1000 MFP) as described previously (FIG. 22).

Immunogenicity of FP Linked to >1000 kDa Oxidized Mannan

A MUC1-specific T cell line was generated by repeated stimulation with oxidized mannan-pTrc followed by sorting of MUC1-specific T cell and expansion. The ability of allogeneic DCs (BC16) pulsed with mannan conjugates to present MUC1-10 to the MUC1-specific T cell line was investigated. >1000 MFP was able to stimulate a MUC1-specific T cell line as shown in FIG. 23. >1000 MFP was more effective in stimulating the T cells than unconjugated FP at the 10 and 20 μg/ml doses.

Example 12

MUC1-VNTR (pTrc)

Conjugation

MUC1-VNTR (pTrc) was conjugated to >1000 kDa oxidized mannan (FIG. 24). Various amounts of pTrc was reacted with >1000 kDa oxidized mannan to ascertain optimal ratio. Conjugates with antigen:mannan ratio 1:40 (½×, lane 5) was used for immunogenicity studies.

Immunogenicity of MUC1-VNTR Conjugated to >1000 kDa Oxidized Mannan

The in vitro immunogenicity of pTrc linked to >1000 kDa oxidized mannan was ascertained via a pTrc (MUC1) T cell line (from donor BC13) recalled with frozen MoDC (frozen, BC17K) (FIG. 25). As shown, pTrc was not effectively processed and presented to the MUC1-specific T cells. However, the >1000 kDa conjugate stimulated MUC1 specific T cells more effectively than unconjugated pTrc. Autologous MoDC pulsed with 20 ng/ml pTrc, >1000 kDa pTrc conjugates were used to recall MUC1 specific CD8 responses from a MUC1-specific T cell line derived from healthy donor BC17K (FIG. 26). >1000 kDa oxidized mannan conjugates efficiently stimulated intracellular IFNγ secretion in CD8 T cells compared to non-conjugated antigen.

Example 13

MART-1

Conjugation

Recombinant MART-1 protein was also linked to >1000 kDa oxidized mannan as described above (FIG. 27). Two types of conjugates were made with MART-1 protein, normal and reduced. The MART-1 protein has several cysteines and is therefore prone to air oxidation and aggregation. To facilitate conjugation, MART-1 was first reduced with DTT and then used in conjugation.

Immunogenicity of MART-1>1000 kDa Oxidized Mannan Conjugates

T Cell Priming and Recall with Peptides

PBMC and MoDC from 2 donors (BC28 and BC29) were used for priming with MART-1 and >1000 kDa oxidized mannan conjugates (20 μg/ml) as described in Example 1. After 1 stimulation, analog and native MART-1 peptide-specific T cell responses were measured using pulsed T2 cells (FIG. 28). BC28 donor T cells primed with >1000 kDa oxidized mannan-MART-1 efficiently responded to analog or native MART-1 peptides presented by T2 cells (FIG. 28). The BC28 and BC29 cultures were re-stimulated with the respective proteins and conjugates and tested for MART-1 protein-specific T cell responses using autologous pulsed MoDC as antigen presenting cells (FIG. 29). The pulsed MoDC were able to recall MART-1-specific CD8 T cell responses in BC28 and BC29 donor T cells primed with >1000 kDa oxidised mannan conjugate. The priming with MART-1>1000 kDa oxidized mannan was more efficient in priming than unconjugated protein.

Example 14

In Vivo Immunogenicity Studies with a Mixture of Inactivated Influenza Virus (H1N1) and >1000 kDa Mannan Influenza Virus and Mice Egg-grown H1N1 (A/New Calcdonia/20/1999) virus was purified by sucrose gradient, concentrated and inactivated with β-propiolactone, to create an influenza zonal pool (IZP) preparation which was kindly provided by Dr Ian Barr, Deputy Director of the WHO Collaborating Centre for Reference and Research on Influenza (North Melbourne, Australia). All mice were female BALB/c supplied by WEHI (Melbourne, Australia), and were 8-10 weeks of age at first immunization.

Generation of H1N1/>1000 kDa Mannan Mixes

H1N1/>1000 kDa mannan mixes were generated by diluting the H1N1 stock (from 2.7 mg/ml) and the >1000 kDa mannan stock (from 14 mg/ml) in sterile PBS, such that the desired dose of each was contained in 50 μl. The >1000 kDa mannan was isolated as described previously.

Immunisations

All immunisations were administered via the intranasal route. While completely anaesthetized (via methoxyfluorane inhalation) and held upright, approximately 5 µl drops were gently pipetted alternately into each nostril.

Serum and BAL (Bronchio-Alveolar-Lavage/Lung-Wash) Collection

Serum was collected by retro-orbital bleed as described. Before collection of BAL, mice were euthanised with a cocktail of ketamine and xylazil. Tissue was removed to expose the upper trachea, and a small incision made therein. With the aid of a blunt needle attached to a 1 ml syringe, 1 ml of PBS was gently flushed into the lungs, and drawn back out.

ELISA Determination of Antibody Titre

ELISAs were performed using the HRP/TMB system. Plates were coated with whole inactivated H1N1 (A/New Caledonia/20/1999) at a concentration of 1 µg/ml. Total anti H1N1 IgG was detected using directly conjugated rat anti-mouse IgG-HRP (GE healthcare, product # RPN1231V) and IgG1, IgG2a and IgA were detected using biotin labeled primary antibodies from Pharmingen (product numbers 553441, 553388 and 556978), and secondary streptavidin-HRP from GE healthcare (product #346480). End-titre was measured as the last value in the titration to remain above the corresponding control value, where the control was calculated as the mean OD values +2SD of naïve mouse sera (3-5 mice) at each titration point.

Groups of 4 BALB/c mice were immunized intranasally with H1N1 (1 μg), or H1N1 mixed with >1000 kDa mannan (100 μg) on days 0, 14. Ten-fourteen days after last immunization, mice serum and lung secretions were analysed for H1N1 specific IgG1, IgG2a and IgA antibodies. As seen in FIG. 30, >1000 kDa mannan enhanced serum IgG1 responses. More importantly >1000 kDa mannan was effective in enhancing serum and lung H1N1-specific IgA.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The present application claims priority from U.S. 61/333,086 filed 10 May 2010, AU 2010901997 filed 10 May 2010 and AU 2010904060 filed 9 Sep. 2010, the entire contents of which are incorporated herein by reference.

REFERENCES

Anumula, Analytical Biochemistry (1994) 220:275
Apostolopoulos et al., Br. J. Cancer (1993) 67:713
Apostolopoulos et al., Vaccine (2000) 18:3174
Apostolopoulos et al., Vaccine (2006) 24:3191
Barreto-Bergter and Gorin, Adv. Carbohydr. Chem. Biochem. (1983) 41:67
Cheever et al., Clin. Cancer Res (2009) 15:5323
Loveland et al., Clin. Cancer Res (2006) 123:869
Monsigny et al., Analytical Biochemistry (1988) 175:525
Pietersz et al., Current Medicinal Chemistry (2006) 13(14): 1591
Sharma et al., Electrophoresis (2003) 24:2733
Sutcliffe et al., Science (1983) 219:660
Tang et al., Immunology (2007) 120:325
Tang et al., Vaccine (2008) 26:3827
Tang et al., Biomaterials (2009) 30:1389
van der Bruggen, et al., Science (1991) 245
Vinogradov et al., Carbohydr. Res. (1998) 307
Wang et al., Journal of Chromatographic Science (2007) 45:200

The invention claimed is:

1. A method for inducing and/or enhancing an immune response in a subject, the method comprising administering to the subject an immunostimulator composition comprising mannans, wherein at least 75% of the mannans are greater than 1000 kDa, and optionally at least one antigen or nucleic acid encoding therefor, wherein the immunostimulatory composition and the at least one antigen or nucleic acid encoding therefor are administered sequentially or simultaneously.

2. The method of claim 1, wherein the subject is a bird or a mammal.

3. The method of claim 2, wherein the mammal is a human.

4. A method for activating macrophages, dendritic cells and/or CTLs in vitro or ex vivo, the method comprising contacting the cells with an immunostimulatory composition comprising mannans, wherein at least 75% of the mannans are eater than 1000 kDa.

* * * * *

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: HLA-A2 epitope peptides specific for
      Melan-A/MART-1 (native)

<400> SEQUENCE: 1

Glu Ala Ala Gly Ile Gly Ile Leu Thr Val
1               5                   10

<210> SEQ ID NO 2
<211> LENGTH: 10
<212> TYPE: PRT
<213> ORGANISM: Artificial Sequence
<220> FEATURE:
<223> OTHER INFORMATION: HLA-A2 epitope peptides specific for
      Melan-A/MART-1 (analog)

<400> SEQUENCE: 2

Glu Leu Ala Gly Ile Gly Ile Leu Thr Val
1               5                   10
```